(12) United States Patent
Ledeboer et al.

(10) Patent No.: US 7,226,919 B2
(45) Date of Patent: Jun. 5, 2007

(54) COMPOSITIONS USEFUL AS INHIBITORS OF PROTEIN KINASES

(75) Inventors: Mark Ledeboer, Acton, MA (US); Robert Davies, Somerville, MA (US); David Messersmith, Somerville, MA (US); Young-Choon Moon, Belle Mead, NJ (US); Michael Mullican, Needham, MA (US)

(73) Assignee: Vertex Pharmaceuticals Inc., Cambridge, MA (US)

( * ) Notice: Subject to any disclaimer, the term of this patent is extended or adjusted under 35 U.S.C. 154(b) by 264 days.

(21) Appl. No.: 10/738,965

(22) Filed: Dec. 17, 2003

(65) Prior Publication Data

US 2004/0186115 A1 Sep. 23, 2004

Related U.S. Application Data

(60) Provisional application No. 60/434,880, filed on Dec. 18, 2002.

(51) Int. Cl.
C07D 413/14 (2006.01)
A61K 31/423 (2006.01)

(52) U.S. Cl. .................. 514/235.8; 514/275; 544/122; 544/296; 544/331

(58) Field of Classification Search ................ 544/122, 544/296, 331; 514/235.8, 275
See application file for complete search history.

(56) References Cited

U.S. PATENT DOCUMENTS

| | | | | |
|---|---|---|---|---|
| 6,093,716 A | 7/2000 | Davis et al. | ................. | 514/253 |
| 6,825,190 B2 | 11/2004 | Moon et al. | ................. | 514/218 |

FOREIGN PATENT DOCUMENTS

| | | |
|---|---|---|
| WO | WO 97/19065 | 5/1997 |
| WO | WO 97/19065 A1 | 5/1997 |
| WO | WO 00/78731 A1 | 12/2000 |
| WO | WO 01/00207 A1 | 1/2001 |
| WO | WO 01/00214 | 1/2001 |
| WO | WO 01/00214 A1 | 1/2001 |
| WO | WO 01/12621 A1 | 2/2001 |
| WO | WO 01/29009 A1 | 4/2001 |
| WO | WO 01/72745 | 10/2001 |
| WO | WO 01/72745 A1 | 10/2001 |
| WO | WO 02/102800 | 12/2002 |

OTHER PUBLICATIONS

Damasio, Alzheimer's Disease and Related Dementias, Cecil Textbook of Medicine, 20th Edition, vol. 2, pp. 1992-1996, 1996.*
Layzer, Degenerative diseases of the Nervous System, Cecil Textbook of Medicine, 20th Edition, vol. 2, pp. 2050-2057, 1996.*
Casanova et al., PubMed Abstract (Rev Neurol 28(9):909-15) May 1999.*
Douglas, Jr. Introduction to Viral Diseases, Cecil Textbook of Medicine, 20th Edition, vol. 2, pp. 1739-1747, 1996.*
Simone, Oncology: Introduction, Cecil Textbook of Medicine, 20th Edition, vol. 1, pp. 1004-1010, 1996.*
Hardt et al., Glycogen Synthase Kinase-3beta A Novel Regulator of Cardiac Hypertrophy and Development, Circulation Research, 90:1055-1063, 2002.*
Traxler, Protein Tyrosine Kinase inhibitors in cancer treatment, Exp. Opin. Ther. Patents, 7(6):571-588, 1997.*
Changelian et al., "Prevention of organ allograft rejection by a specific janus kinase 3 inhibitor," Science, 302:875-878, (2003).
Malaviya et al., "Treatment of allergic asthma by targeting janus kinase 3-dependent leukotriene synthesis in mast cells with 4-(3',5'—dibromo-4'-hydroxyphenyl)amino-6,7-dimethoxyquinazoline (WHI-P97)," The Journal of Pharmacology and Experimental Therapeutics, 295(3):912-926, (2000).
Trieu et al., "A specific inhibitor of janus kinase-3 increases survival in a transgenic mouse model of amyotrophic lateral sclerosis," Biochemical and Biophysical Research Communications, 267:22-25, (2000).
Zimmerman et al., "Potent and selective inhibitors of the Abl-kinase: phenylamino-pyrimidine (PAP) derivatives," Bioorg. Med. Chem. Lett., 7(2):187-192, (1997)
Duhe et al., "Negative regulation of janus kinases", Cell Biochemistry and Biophysics, 34(1):17-59, (2001).
Rane et al., "Janus kinases: components of multiple signaling pathways" Oncogene 19(49):5662-79, (2000).
Kim et al., "GSK3, a master switch regulating cell-fate specification and tumorigenesis", Current Ioinion in Genetics & Development, 10(5):508-514, (2000).

* cited by examiner

Primary Examiner—Deepak Rao
(74) Attorney, Agent, or Firm—Karen E. Brown

(57) ABSTRACT

The present invention provides a compound of formula (I):

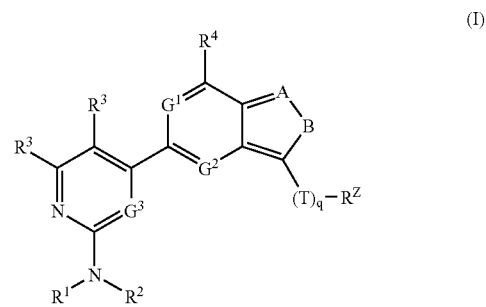

or a pharmaceutically acceptable salt thereof. These compounds are inhibitors of protein kinases, particularly inhibitors of GSK-3, JAK-3, FLT-3, PIM-1, SYK, or PDK-1 mammalian protein kinases. The invention also provides pharmaceutically acceptable compositions comprising the compounds of the invention and methods of utilizing those compounds and compositions in the treatment of various protein kinase mediated disorders.

31 Claims, No Drawings

COMPOSITIONS USEFUL AS INHIBITORS OF PROTEIN KINASES

CROSS-REFERENCE TO RELATED APPLICATIONS

The present application claims priority under 35 U.S.C. §119 to U.S. Provisional Application No. 60/434,880, filed Dec. 18, 2002, entitled "Compositions Useful as Inhibitors of Protein Kinases, the entire contents of which is hereby incorporated by reference.

TECHNICAL FIELD OF THE INVENTION

The present invention relates to inhibitors of protein kinases. The invention also provides pharmaceutical compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book*, I and II, Academic Press, San Diego, Calif.: 1995). Protein kinases are thought to have evolved from a common ancestral gene due to the conservation of their structure and catalytic function. Almost all kinases contain a similar 250–300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576–596; Knighton et al., *Science* 1991, 253, 407–414; Hiles et al., *Cell* 1992, 70, 419–429; Kunz et al., *Cell* 1993, 73, 585–596; Garcia-Bustos et al., *EMBO J.* 1994, 13, 2352–2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β isoforms that are each encoded by distinct genes [Coghlan et al., *Chemistry & Biology* 2000, 7, 793–803; and Kim and Kimmel, *Curr. Opinion Genetics Dev.,* 2000 10, 508–514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117–130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor eIF2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455–8459; Cross et al., *Biochem. J.* 1994, 303, 21–26); Cohen, *Biochem. Soc. Trans.* 1993, 21, 555–567; and Massillon et al., *Biochem J.* 1994, 299, 123–128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is also associated with Alzheimer's disease. This disease is characterized by the well-known β-amyloid peptide and the formation of intracellular neurofibrillary tangles. Aβ peptides are derived from the amyloid precursor protein (APP) by sequential proteolysis, catalysed by the aspartyl protease BACE2, followed by presenilin-dependent γ-secretase cleavage. It has been demonstrated that antibodies against β-amyloid plaques can slow cognitive decline in patients with Alzheimer's disease (Hock et al., *Neuron,* 2003, 38, 547–554), and thus other β-amyloid-lowering strategies (e.g., the development of agents capable of inhibiting β-amyloid peptide) would be useful in the treatment of Alzheimer's disease and other psychotic and neurodegenerative disorders. Additionally, the neurofibrillary tangles contain hyperphosphorylated Tau protein, in which Tau is phosphorylated on abnormal sites, and thus agents capble of inhibiting the hyperphosphorylation of Tau protein would be useful in the treatment of Alzherimer's disease and other psychotic and neurodegenerative disorders.

GSK-3 is known to phosphorylate these abnormal sites in cell and animal models. Furthermore, inhibition of GSK-3 has been shown to prevent hyperphosphorylation of Tau in cells [Lovestone et al., *Current Biology* 1994, 4, 1077–86; and Brownlees et al., *Neuroreport* 1997, 8, 3251–55]. Therefore, GSK-3 activity promotes generation of the neurofibrillary tangles and the progression of Alzheimer's disease. It has also been shown that GSK-3 facilitates APP processing and that a GSK-3 inhibitor (lithium) inhibits of the generation of Aβ peptides through the inhibition of GSK-3 (Phiel et al. *Nature* 2003, 423, 435–439). Thus, the development of inhibitors of GSK-3 would be useful for the reduction of the formation of amyloid plaques and neurofibrillry tangles, the pathological hallmarks of Alzheimer's Disease, and would also be useful for the treament of other psychotic and neurodegenerative disorders.

Another substrate of GSK-3 is β-catenin, which is degradated after phosphorylation by GSK-3. Reduced levels of β-catenin have been reported in schizophrenic patients and have also been associated with other diseases related to increase in neuronal cell death [Zhong et al., *Nature* 1998, 395, 698–702; Takashima et al., *PNAS* 1993, 90, 7789–93; and Pei et al., *J. Neuropathol. Exp* 1997, 56, 70–78].

GSK-3 activity is also associated with stroke [Wang et al., *Brain Res* 2000, 859, 381–5; Sasaki et al., *Neurol Res* 2001, 23, 588–92; Hashimoto et al., *J. Biol. Chem* 2002, 277, 32985–32991].

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank Mol. Med. 5: 432–456 (1999) & Seidel, et al, Oncogene 19: 2645–2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al, Blood 96: 2172–2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, Nature 346: 274–276 (1990) & Galli, N. Engl. J. Med., 328: 257–265 (1993)]. A crucial role for JAK3 in IgE receptor-mediated mast cell responses in vitro and in vivo has been established [Malaviya, et al, Biochem. Biophys. Res. Commun. 257: 807–813 (1999)]. In addition, the prevention of type I hypersensitivity reactions, including anaphylaxis, mediated by mast cell-activation through inhibition of JAK3 has also been reported [Malaviya et al, J. Biol. Chem. 274:27028–27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immunosuppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, transpl. proc. 33: 3268–3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner, et al, J. Immunol. 164: 3894–3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu, et al, Biochem. Biophys. Res. Commun. 267: 22–25 (2000)].

Signal transducer and activator of transcription (STAT) proteins are activated by, among others, the JAK family kinases. Results from a recent study suggested the possibility of intervention in the JAK/STAT signaling pathway by targeting JAK family kinases with specific inhibitors for the treatment of leukemia [Sudbeck, et al, Clin. Cancer Res. 5: 1569–1582 (1999)]. JAK3 specific compounds were shown to inhibit the clonogenic growth of JAK3-expressing cell lines DAUDI, RAMOS, LC1; 19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al, EMBO J. 17: 5321–5333 (1998)].

Inhibition of JAK3 and TYK2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al, Proc. Nat. Acad. Sci. U.S.A. 94: 6764–6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, J. Immunol. 159: 5206–5210 (1997)]. In addition, IL-6-mediated STAT3 activation was blocked by an inhibitor of JAK, leading to sensitization of myeloma cells to apoptosis [Catlett-Falcone, et al, Immunity 10:105–115 (1999)].

PIM-1 is the protooncogene activated by murine leukemia virus (Provirus Integration site for Moloney murine leukemia virus) [Cuypers, H. T., et al., Cell 37, 141–150 (1984)]. The expression of the protoconcogene produces a non-transmembrane serine/threonine kinase of 313 residues, including a kinase domain consisting of 253 amino acid residues. Two isoforms are known through alternative initiation (p44 and p33) [Saris, C. J. M., et al., EMBO J., 10, 655–664 (1991)]. Two PIM-1 homologs have been described [Baytel, D., Biochim Biophys Acta 1442, 274–85

(1998); Feldman, J., et al., J Biol Chem 273, 16535–16543 (1998)]. PIM-2 and PIM-3 are respectively 58% and 69% identical to Pim-1 at the amino acid level. PIM-1 is highly expressed in the liver and spleen during hematopoiesis, and expression is induced by cytokines such as GM-CSF, G-SCF, IL-3, IF-α, and IL-6 [Lilly, M., et al., Oncogene 7, 727–732 (1992); Sato, N., et al., EMBO J. 12, 4181–4189 (1993); Jaster, R.,et al., Cell Signal 11, 331–335 (1999); Matikainen, S., et al., Blood 93, 1980–1991 (1999)].

PIM-1 has been implicated in lymphoma development. Induced expression of PIM-1 and the protooncogene c-myc synergize to increase the incidence of lymphomagenesis [Breuer M., et al., Nature 340, 61–63 (1989); van Lohuizen M., et al., Cell 65, 737–52 (1991)]. PIM-1 functions in cytokine signaling pathways and has been shown to play a role in T cell development [Schmidt, T., et al., EMBO J 17, 5349–5359 (1998); Jacobs, H., et al., JEM 190, 1059–1068 (1999)]. Signaling through gp130, a subunit common to receptors of the IL-6 cytokine family, activates the transcription factor STAT3 and can lead to the proliferation of hematopoietic cells [Hirano, T., et al., Oncogene 19, 2548–2556 (2000)]. A kinase-active PIM-1 appears to be essential for the gp130-mediated STAT3 proliferation signal. In cooperation with the c-myc PIM-1 can promote STAT3-mediated cell cycle progression and antiapoptosis [Shirogane, T., et al., Immunity 11, 709–719 (1999)]. PIM-1 also appears to be necessary for IL-3-stimulated growth in bone marrow-derived mast cells [Domen J., et al., Blood 82, 1445–52 (1993)] and survival of FDCP1 cells after IL-3 withdrawal [Lilly, M., et al., Oncogene 18, 4022–4031 (1999)].

Additionally, control of cell proliferation and survival by PIM-1 may be effected by means of its phosphorylation of the well established cell cycle regulators cdc25 [Mochizuki , T., et al., J Biol Chem 274, 18659–18666 (1999)] and/or p21(Cip1/WAF1)[ Wang, Z., et al., Biochim Biophys Acta 1593, 45–55 (2002)] or phosphorylation of heterochromatin protein 1, a molecule involved in chromatin structure and transcriptional regulation [Koike N., et al., FEBS Lett 467, 17–21 (2000)].

Both FLT-3 and c-Kit belong to a family of receptor tyrosine kinases, including PDGF-receptor and c-Fms [Scheijen, B, Griffin J D, Oncogene, 21, 3314–3333 (2002)]. FLT-3 and c-Kit regulate maintenance of stem cell/early progenitor pools as well the development of mature lymphoid and myeloid cells [Lyman, S, Jacobsen, S, Blood, 91, 1101–1134 (1998)]. Both receptors contain an intrinsic kinase domain that is activated upon ligand mediated dimerization of the receptors. Upon activation, the kinase domain induces autophosphorylation of the receptor as well as the phosphorylation of various cytoplasmic proteins that help propogate the activation signal leading to growth, differentiation and survival. Some of the downstream regulators of FLT-3 and c-Kit receptor signaling include, PLCγ, PI3-kinase, Grb-2, SHIP and Src related kinases [Scheijen, B, Griffin J D, Oncogene, 21, 3314–3333 (2002)]. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-33 or c-Kit can contribute to the malignant phenotype [Scheijen, B, Griffin J D, Oncogene, 21, 3314–3333 (2002)].

The 3-phosphoinositide-dependent protein kinase-I (PDK1) plays a key role in regulating the activity of a number of kinases belonging to the AGC subfamily of protein kinases (Alessi, D. et al., Biochem. Soc. Trans, 2001, 29, 1). These include isoforms of protein kinase B (PKB, also known as Akt), p70 ribosomal S6 kinase (S6K) (Avruch, J. et al., prog. Mol. Subcell. Biol., 2001, 26, 115), and p90 ribosomal S6 kinase (Frodin, M. et al., EMBO, 2000, 19, 2924). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation (Lawlor, M. A. et al., J. Cell Sci., 2001, 114, 2903: Lawlor, M. A. et al., EMBO J., 2002 21, 3728). PDK1 is a 556 amino acid protein, with an N-terminal catalytic domain and a C-terminal pleckstrin homology (PH) domain, which activates its substrates by phosphorylating these kinases at their activation loop (Belham, C. et al., Curr. Biol., 1999 9, R93). Many human cancers including prostate and NSCL have elevated PDK1 signaling pathway function resulting from a number of distinct genetic events such as PTEN mutations or over-expression of certain key regulatory proteins (Graff, J. R., Expert Opin. Ther. Targets, 2002, 6, 103: Brognard, J., et al., Cancer Res., 2001, 61, 3986). Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., Curr. Biol., 2000, 10, 1439). Consequently the design of ATP binding site inhibitors of PDK1 offers, amongst other treatments, an attractive target for cancer chemotherapy.

Syk is a tyrosine kinase that plays a critical role in FcεRI mediated mast cell degranulation and eosiniphil activation. Accordingly, Syk kinase is implicated in various allergic disorders, in particular asthma. It has been shown that Syk binds to the phosphorylated gamma chain of the FcεRI receptor via N-terminal SH2 domains and is essential for downstream signaling [Taylor et al, Mol Cell Biol 1995; 15:4149].

Inhibition of eosinophil apoptosis has been proposed as key mechanisms for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense) [Yousefi et al, J Exp Med 1996;183:1407].

The role of Syk in FcγR dependent and independent response in bone marrow derived macrophages has been determined by using irradiated mouse chimeras reconstituted with fetal liver cells from Syk −/− embryos. Syk deficient macrophages were defective in phagocytosis induced by FcγR but showed normal phagocytosis in response to complement [Kiefer et al, Mol Cell Biol 1998;

18:4209]. It has also been reported that aerosolized Syk antisense suppresses Syk expression and mediator release from macrophages [Stenton et al, J Immunology 2000; 164: 3790].

There is a continued need to find new therapeutic agents to treat human diseases. Accordingly, there is a great need to develop inhibitors of GSK-3, JAK, FLT-3, PIM-1, SYK, and PDK-1 protein kinases that are useful in treating various diseases or conditions associated with GSK-3, JAK, FLT-3, PIM-1, SYK, and PDK-1 activation, particularly given the inadequate treatments currently available for the majority of these disorders.

SUMMARY OF THE INVENTION

It has now been found that compounds of this invention, and pharmaceutically acceptable compositions thereof, are effective as inhibitors of protein kinases. In certain embodiments, these compounds are effective as inhibitors of GSK-3, JAK, FLT-3, SYK, PIM-1, or PDK-1 protein kinases. These compounds have the general formula I:

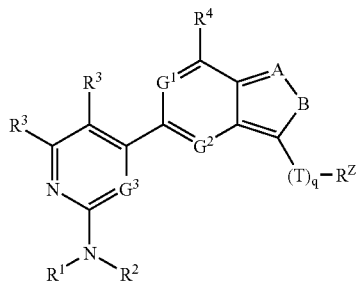

or a pharmaceutically acceptable salt thereof, wherein $R^1$, $R^2$, $R^3$, $R^4$, T, q, $R^Z$, $G^1$, $G^2$, $G^3$, A, and B are as defined below.

These compounds and pharmaceutical compositions thereof are useful for treating or preventing a variety of disorders or conditions, including, but not limited to, heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, neurodegenerative or neurological disorders, or viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer, liver disease including hepatic ischemia, heart disease such as myocardial infarction and congestive heart failure, pathologic immune conditions involving T cell activation, and neurodegenerative disorders.

DETAILED DESCRIPTION OF THE INVENTION

I. General Description of Compounds of the Invention:
The present invention relates to a compound of formula I:

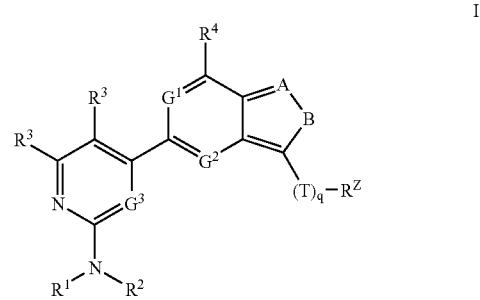

or a pharmaceutically acceptable salt thereof, wherein:
A-B is N—O or O—N;
$R^1$ and $R^2$ are each independently selected from hydrogen, or $(U)_p$—$R^5$, wherein p is 0 or 1, U is an optionally substituted $C_1$–$C_6$ alkylidene chain wherein up to two non-adjacent methylene units of U are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR, and $R^5$ is an optionally substituted group selected from optionally substituted $C_{1-10}$aliphatic, an aryl group selected from a 5–6 membered monocyclic or an 8–10 membered bicyclic ring having 0–5 heteroatoms independently selected from nitrogen, oxygen, or sulfur; a 3–8-membered saturated or partially unsaturated monocyclic ring having 0–3 heteroatoms independently selected from nitrogen, oxygen, or sulfur, or an 8–10-membered saturated or partially unsaturated bicyclic ring system having 0–5 heteroatoms independently selected from nitrogen, oxygen, or sulfur; or $R^1$ and $R^2$ taken together with the nitrogen atom form an optionally substituted 5–8 membered heterocyclyl or heteroaryl ring having 1–3 heteroatoms independently selected from nitrogen, oxygen, or sulfur, wherein $R^1$ and $R^2$ are each independently optionally substituted with up to five substituents selected from Q-$R^X$; wherein Q is a bond or is an optionally substituted $C_1$–$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^X$ is independently selected from R', halogen, $NO_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';
$G^1$ and $G^2$ are each independently N or CR$^4$;
$G^3$ is N or CR$^3$;
each occurrence of $R^3$ and $R^4$ is independently selected from R, halogen, CN, OR, N(R)$_2$, SR, C(=O)R, CO$_2$R, CONR$_2$, NRC(=O)R, NRCO$_2$(C$_{1-6}$ aliphatic), OC(=O)R, SO$_2$R, S(=O)R, SO$_2$NR$_2$, or NRSO$_2$(C$_{1-6}$ aliphatic);
T is an optionally substituted $C_{1-4}$ alkylidene chain wherein one methylene unit of T is optionally replaced by O, NR, NRCO, NRCONR, NRCO$_2$, CO, CO$_2$, CONR, OC(O)NR, SO$_2$, SO$_2$NR, NRSO$_2$, NRSO$_2$NR, C(O)C(O), or C(O)CH$_2$C(O); q is 0 or 1;

R$^Z$ is R, CN, halogen, or Cy;

Cy is an optionally substituted aryl or heteroaryl group selected from a 5–6 membered monocyclic or an 8–10 membered bicyclic ring having 0–5 heteroatoms independently selected from nitrogen, oxygen, or sulfur; or is an optionally substituted group selected from a 3–8-membered saturated or partially unsaturated monocyclic ring having 0–3 heteroatoms independently selected from nitrogen, oxygen, or sulfur, or an 8–10-membered saturated or partially unsaturated bicyclic ring system having 0–5 heteroatoms independently selected from nitrogen, oxygen, or sulfur, wherein Cy is optionally substituted with up to five substituents selected from Z-R$^Y$; wherein Z is a bond or is a C$_1$–C$_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR; and each occurrence of R$^Y$ is independently selected from R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, C(O)C(O)R', or C(O)CH$_2$C(O)R';

each occurrence of R is independently selected from hydrogen or an optionally substituted C$_{1-8}$ aliphatic group, or two R on the same nitrogen are taken together with the nitrogen to form an optionally substituted 5–8 membered heterocyclyl or heteroaryl ring having 1–3 heteroatoms independently selected from nitrogen, oxygen, or sulfur; and each occurrence of R' is independently selected from hydrogen or an optionally substituted group selected from C$_{1-8}$ aliphatic, C$_{6-10}$ aryl, a heteroaryl ring having 5–10 ring atoms, or a heterocyclyl ring having 3–10 ring atoms, or wherein two R' on the same nitrogen are taken together with the nitrogen to form an optionally substituted 5–8 membered heterocyclyl or heteroaryl ring having 1–3 heteroatoms independently selected from nitrogen, oxygen, or sulfur, provided that when R$^Z$ is Cy, and Cy is an optionally substituted 5–6 membered monocyclic or an 8–10 membered bicyclic aryl ring having 0 heteroatoms, then q is 1.

In certain embodiments, for compounds of formula I, when R$^Z$ is Cy and Cy is an optionally substituted aryl group selected from a 5–6 membered monocyclic or an 8–10 membered bicyclic ring having 0–5 heteroatoms independently selected from nitrogen, oxygen, or sulfur, then q is 1.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1–20 aliphatic carbon atoms. In some embodiments, aliphatic groups contain 1–10 aliphatic carbon atoms. In other embodiments, aliphatic groups contain 1–8 aliphatic carbon atoms. In still other embodiments, aliphatic groups contain 1–6 aliphatic carbon atoms, and in yet other embodiments aliphatic groups contain 1–4 aliphatic carbon atoms. In some embodiments, "cycloaliphatic" (or "carbocycle" or "cycloalkyl") refers to a monocyclic C$_3$–C$_8$ hydrocarbon or bicyclic C$_8$–C$_2$ hydrocarbon that is completely saturated or that contains one or more units of unsaturation, but which is not aromatic, that has a single point of attachment to the rest of the molecule wherein any individual ring in said bicyclic ring system has 3–7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R$^o$; —OR$^o$; —SR$^o$; phenyl (Ph) optionally substituted with R$^o$; —O(Ph) optionally substituted with R$^o$; —(CH$_2$)$_{1-2}$(Ph), optionally substituted with R$^o$; —CH=CH(Ph), optionally substituted with R$^o$; —NO$_2$; —CN; —N(R$^o$)$_2$; —NR$^o$C(O)R$^o$; —NR$^o$C(S)R$^o$; —NR$^o$C(O)N(R$^o$)$_2$; —NR$^o$C(S)N(R$^o$)$_2$; —NR$^o$CO$_2$R$^o$; —NR$^o$NR$^o$C(O)R$^o$; —NR$^o$NR$^o$C(O)N(R$^o$)$_2$; —NR$^o$NR$^o$CO$_2$R$^o$; —C(O)C(O)R$^o$; —C(O)CH$_2$C(O)R$^o$; —CO$_2$R$^o$; —C(O)R$^o$; —C(S)R$^o$; —C(O)N(R$^o$)$_2$; —C(S)N(R$^o$)$_2$; —OC(O)N(R$^o$)$_2$; —OC(O)R$^o$; —C(O)N(OR$^o$) R$^o$; —C(NOR$^o$) R$^o$; —S(O)$_2$R$^o$; —S(O)$_3$R$^o$; —SO$_2$N(R$^o$)$_2$; —S(O)R$^o$; —NR$^o$SO$_2$N(R$^o$)$_2$; —NR$^o$SO$_2$R$^o$; —N(OR$^o$)R$^o$; —C(=NH)—N(R$^o$)$_2$; —P(O)$_2$R$^o$; —PO(R$^o$)$_2$; —OPO(R$^o$)$_2$; —(CH$_2$)$_{0-2}$NHC(O)R$^o$; phenyl (Ph) optionally substituted with R$^o$; —O(Ph) optionally substituted with R$^o$; —(CH$_2$)$_{1-2}$(Ph), optionally substituted with R$^o$; or —CH=CH(Ph), optionally substituted with R$^o$; wherein each independent occurrence of R$^o$ is selected from hydrogen, optionally substituted C$_{1-6}$ aliphatic, an unsubstituted 5–6 membered heteroaryl or heterocyclic ring, phenyl, —O(Ph), or —CH$_2$(Ph), or, notwithstanding the definition above, two independent occurrences of R$^o$, on the same substituent or different substituents, taken together with the atom(s) to which each R$^o$ group is bound, to form an optionally substituted 3–12 membered saturated, partially unsaturated, or fully unsaturated monocyclic or bicyclic ring having 0–4 heteroatoms independently selected from nitrogen, oxygen, or sulfur.

Optional substituents on the aliphatic group of R$^o$ are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R$^o$ is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic group.

Unless otherwise defined above and herein, optional substituents on the nitrogen of a non-aromatic heterocyclic ring are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5–6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form an optionally substituted 3–12 membered saturated, partially unsaturated, or fully unsaturated monocyclic or bicyclic ring having 0–4 heteroatoms independently selected from nitrogen, oxygen, or sulfur.

Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R$^o$ (or R$^+$, R, R' or any other variable similarly defined herein), are taken together with the atom(s) to which they are bound to form an optionally substituted 3–12 membered saturated, partially unsaturated, or fully unsaturated monocyclic or bicyclic ring having 0–4 heteroatoms independently selected from nitrogen, oxygen, or sulfur.

Exemplary rings that are formed when two independent occurrences of R$^o$ (or R$^+$, R, R' or any other variable similarly defined herein), are taken together with the atom(s) to which each variable is bound include, but are not limited to the following: a) two independent occurrences of R° (or R+, R, R' or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R+, R, R' or any other variable similarly defined herein) that are bound to different atoms and are taken together with both of those atoms to form a ring, for example where a phenyl group is substituted with two occurrences of

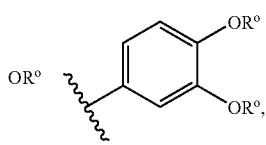

these two occurrences of R° are taken together with the oxygen atoms to which they are bound to form a fused 6-membered oxygen containing ring:

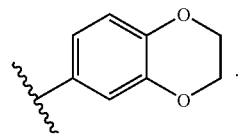

It will be appreciated that a variety of other rings can be formed when two independent occurrences of R° (or R+, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds:

One embodiment of the present invention relates to compounds that are 1,2-benzisoxazoles, represented by formula I-A shown below. Another embodiment of this invention relates to compounds that are 2,1-benzisoxazoles, represented by formula I-B shown below:

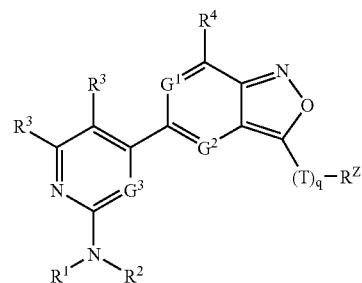

I-A

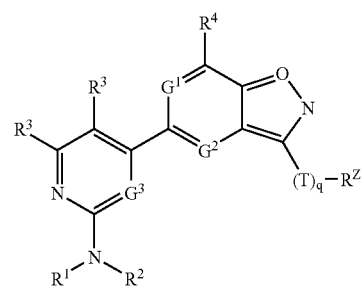

I-B

As described generally above, R$^1$ and R$^2$ are each independently selected from hydrogen, or (U)$_p$—R$^5$, wherein p is 0 or 1, U is an optionally substituted C$_1$–C$_6$ alkylidene chain wherein up to two non-adjacent methylene units of U are optionally replaced by CO, CO$_2$, COCO, CONR, OCONR, NRNR, NRNRCO, NRCO, NRCO$_2$, NRCONR, SO, SO2, NRSO$_2$, SO$_2$NR, NRSO$_2$NR, O, S, or NR, and R$^5$ is an optionally substituted group selected from optionally substituted C$_{1-10}$ aliphatic, an aryl group selected from a 5–6 membered monocyclic or an 8–10 membered bicyclic ring having 0–5 heteroatoms independently selected from nitrogen, oxygen, or sulfur; a 3–8-membered saturated or partially unsaturated monocyclic ring having 0–3 heteroatoms independently selected from nitrogen, oxygen, or sulfur, or an 8–10-membered saturated or partially unsaturated bicyclic ring system having 0–5 heteroatoms independently selected from nitrogen, oxygen, or sulfur; or R$^1$ and R$^2$ taken together with the nitrogen atom form an optionally substituted 5–8 membered heterocyclyl or heteroaryl ring having 1–3 heteroatoms independently selected from nitrogen, oxygen, or sulfur.

In certain preferred embodiments, one of R$^1$ or R$^2$ is (U)$_p$—R$^5$, and R$^5$ is an optionally substituted aryl or heteroaryl group selected from:

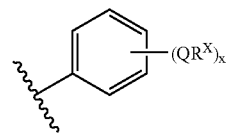

a-i

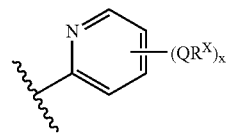

b-i

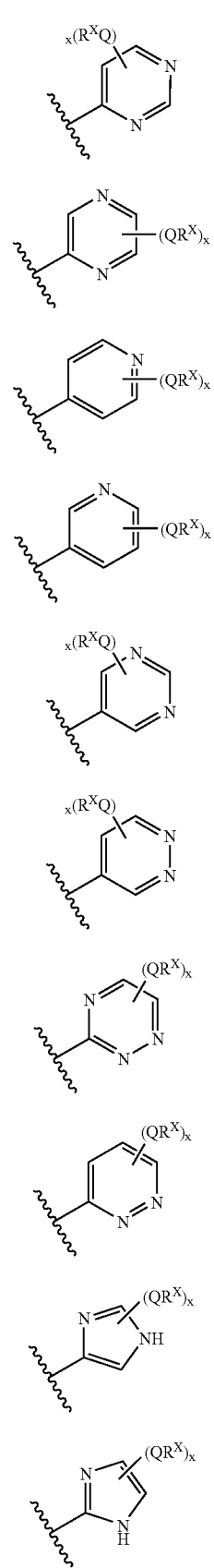
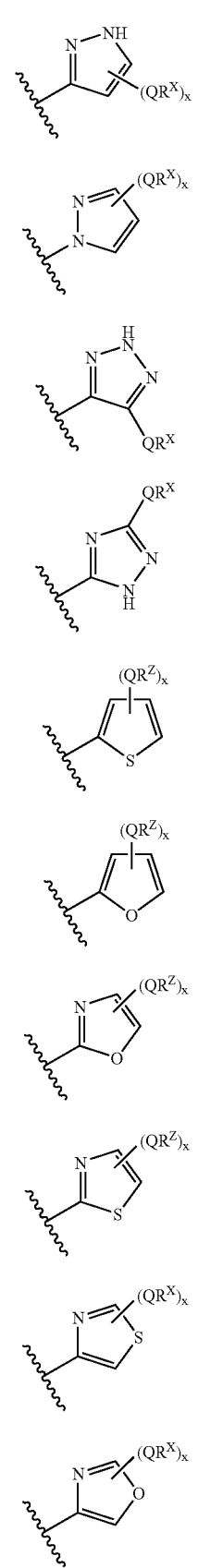

-continued
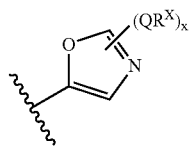 w-i
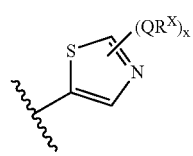 x-i
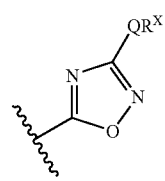 y-i
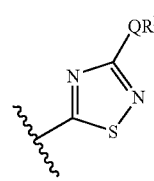 z-i
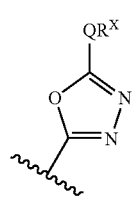 aa-i
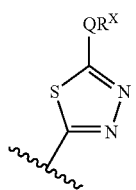 bb-i
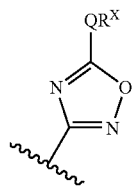 cc-i
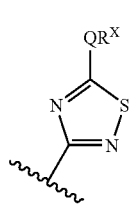 dd-i
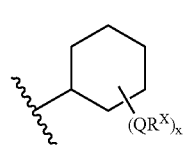 ee-i
-continued
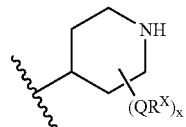 ff-i
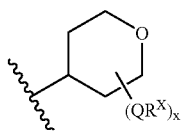 gg-i
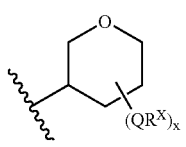 hh-i
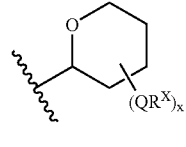 ii-i
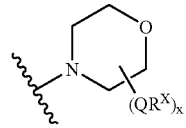 jj-i
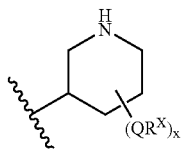 kk-i
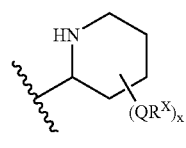 ll-i
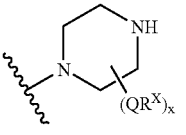 mm-i
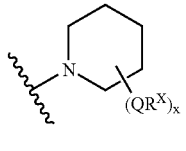 nn-i
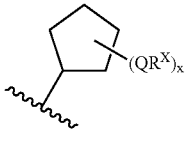 oo-i
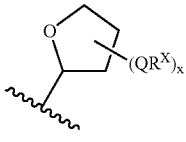 pp-i qq-i

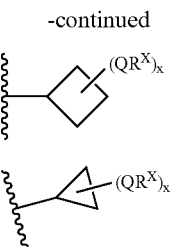

rr-i wherein any substitutable carbon or nitrogen is optionally substituted, wherein x is 0–5, and Q and $R^X$ are as defined generally above and herein.

In more preferred embodiments, $R^1$ is $(U)_p$—$R^5$, wherein U and p are as defined generally above and herein; $R^5$ is any one of a-i through z-i; and $R^2$ is hydrogen.

In other preferred embodiments, $R^2$ is hydrogen; $R^1$ is $(U)_p$—$R^5$, wherein U and p are as defined generally above and herein; and $R^5$ is any one of:

a-i

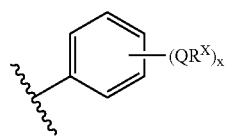

b-i

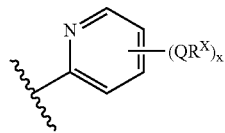

c-i

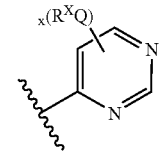

d-i

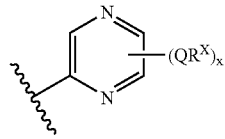

e-i

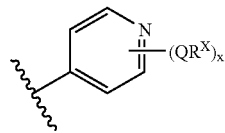

f-i

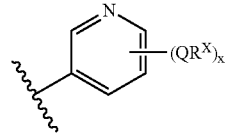

g-i

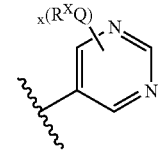

h-i

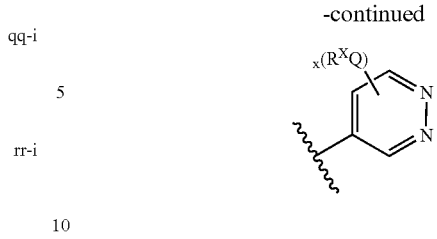

In still other preferred embodiments $R^2$ is hydrogen, and $R^1$ is $(U)_p$—$R^5$, wherein U and p are as defined generally above and herein, and $R^5$ is a-i, b-i, e-i, or f-i.

In most preferred embodiments, $R^2$ is hydrogen; $R^1$ is $(U)_p$—$R^5$, wherein U and p are as defined generally above and herein; and $R^5$ is a-i.

In certain embodiments, p is 0 and $R^5$ is directly attached to the ring system.

In certain other embodiments, p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—. In more preferred embodiments, when p is 1, U is —CH$_2$—, —CO—, —CO(CH$_2$)O—, —CO(CH$_2$)$_2$—, CO(NH)—or —CO(O)—.

As described generally above, $R^Z$ is R, CN, halogen, or Cy, and Cy is an optionally substituted aryl or heteroaryl group selected from a 5–6 membered monocyclic or an 8–10 membered bicyclic ring having 0–5 heteroatoms independently selected from nitrogen, oxygen, or sulfur; or is an optionally substituted group selected from a 3–8-membered saturated or partially unsaturated monocyclic ring having 0–3 heteroatoms independently selected from nitrogen, oxygen, or sulfur, or an 8–10-membered saturated or partially unsaturated bicyclic ring system having 0–5 heteroatoms independently selected from nitrogen, oxygen, or sulfur. In certain preferred embodiments, $R^Z$ is Cy, and Cy is an optionally substituted group selected from:

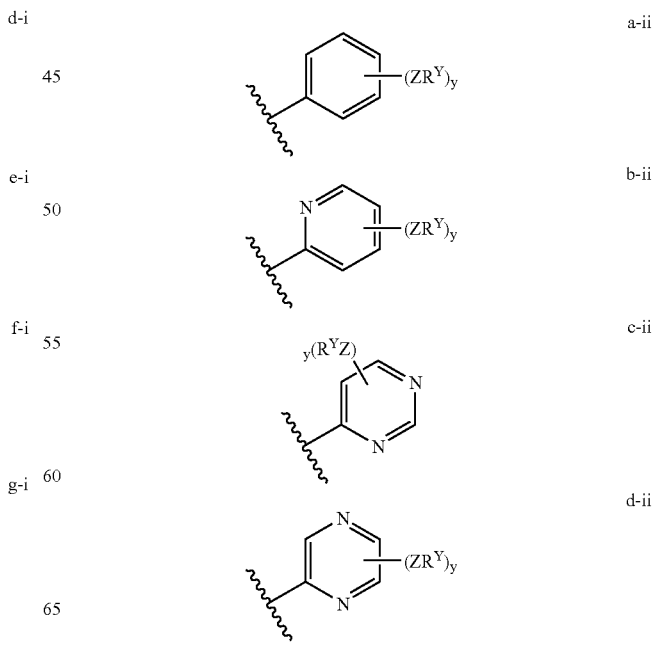

-continued
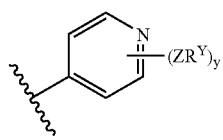 e-ii
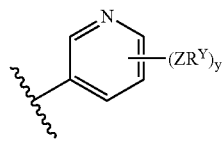 f-ii
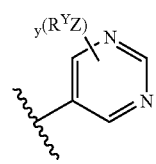 g-ii
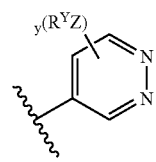 h-ii
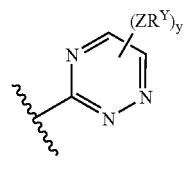 i-ii
 j-ii
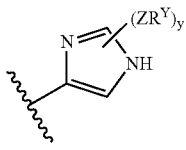 k-ii
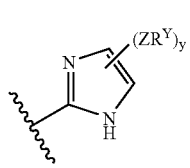 l-ii
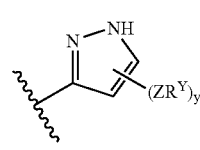 m-ii
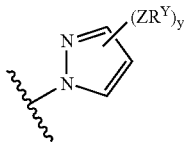 n-ii
-continued
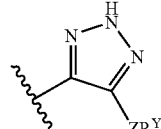 o-ii
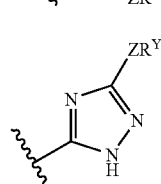 p-ii
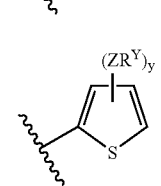 q-ii
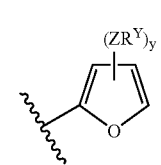 r-ii
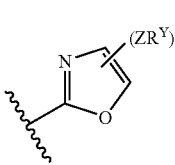 s-ii
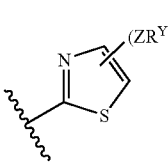 t-ii
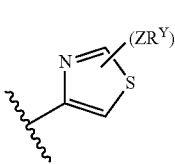 u-ii
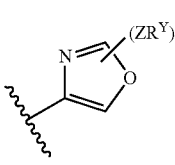 v-ii
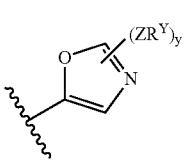 w-ii
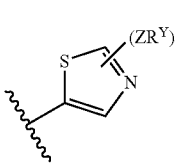 x-ii

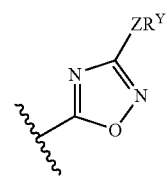 y-ii
 z-ii
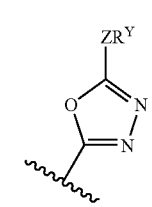 aa-ii
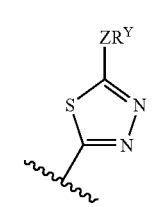 bb-ii
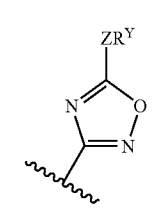 cc-ii
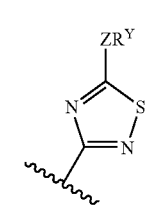 dd-ii
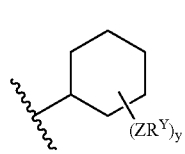 ee-ii
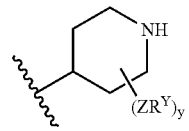 ff-ii
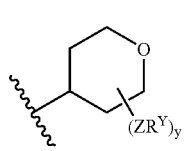 gg-ii
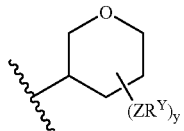 hh-ii
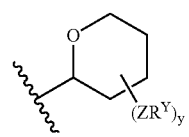 ii-ii
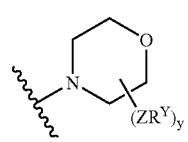 jj-ii
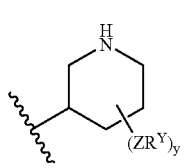 kk-ii
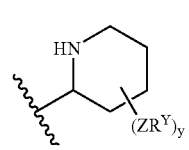 ll-ii
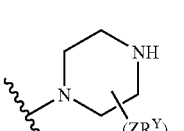 mm-ii
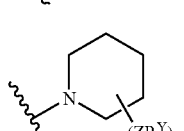 nn-ii
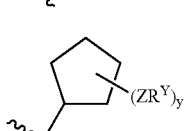 oo-ii
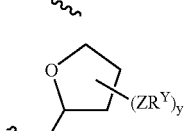 pp-ii
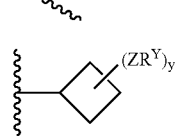 qq-ii
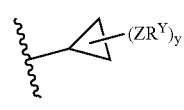 rr-ii
wherein any substitutable nitrogen or carbon atom is optionally substituted, wherein y is 0–5 and $ZR^Y$ is described generally above and herein.

In more preferred embodiments, Cy is a-ii, b-ii, c-ii, e-ii, f-ii, g-ii, or oo-ii.

In certain other embodiments, Cy is any one of i-ii, j-ii, k-ii, l-ii, m-ii, n-ii, o-ii, p-ii, q-ii, r-ii, s-ii, t-ii, u-ii, v-ii, x-ii, y-ii, z-ii, aa-ii, bb-ii, cc-ii, dd-ii, ee-ii, ff-ii, gg-ii, hh-ii, ii-ii, jj-ii, kk-ii, ll-ii, mm-ii, nn-ii, oo-ii, pp-ii, qq-ii, or rr-ii.

In certain preferred embodiments, q is 0 and T is absent.

In certain other preferred embodiments, q is 1 and preferred T groups, when present, are selected from —CH$_2$—, —CH$_2$CH$_2$—, —CH$_2$CH$_2$CH$_2$—, —CH$_2$CH$_2$CH$_2$CH$_2$—, —C≡C—, —CH=CH—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—. In more preferred embodiments, when q is 1, T is —CH$_2$—, —CO—, —CO(CH$_2$)O—, —CO(CH$_2$)$_2$—, CO(NH)— or —CO(O)—.

In preferred embodiments, QR$^X$ and ZR$^Y$ groups are each independently halogen, CN, NO$_2$, or an optionally substituted group selected from C$_{1-4}$alkyl, aryl, aralkyl, —N(R')$_2$, CH$_2$N(R')$_2$, —OR', CH$_2$OR', —SR', CH$_2$SR', COOR', or —S(O)$_2$N(R')$_2$. In more preferred embodiments, QR$^X$ and ZR$^Y$ groups are each independently Cl, Br, F, CN, COOH, —N(CH$_3$)$_2$, —OH, CH$_2$OH, SO$_2$NH$_2$, or an optionally substituted group selected from C$_{1-4}$alkoxy, phenyl, phenyloxy, benzyl, or benzyloxy. Most preferred QR$^X$ and ZR$^Y$ groups include those shown below in Table 1.

As described generally above, each occurrence of R$^3$ and R$^4$ is independently R, halo, CN, OR, N(R)$_2$, SR, C(=O)R, CO$_2$R, CONR$_2$, NRC(=O)R, NRCO$_2$(C$_{1-6}$ aliphatic), OC(=O)R, SO$_2$R, S(=O)R, SO$_2$NR$_2$, or NRSO$_2$(C$_{1-6}$ aliphatic). In more preferred embodiments, each occurrence of R$^3$ is selected from hydrogen or a C$_{1-4}$ alkyl group. In other preferred embodiments, each occurrence of R$^3$ is hydrogen. In certain preferred embodiments, each occurrence of R$^4$ is selected from hydrogen, halo, O(C$_{1-4}$ alkyl), or a C$_{1-4}$ alkyl group. In other preferred embodiments, each occurrence of R$^4$ is hydrogen.

It will be appreciated that for compounds as described above, certain additional compounds are of special interest. For example, in certain exemplary embodiments, G$^1$ and G$^2$ are each CR$^4$, and G$^3$ is N, and compounds have general formula II-A or II-B:

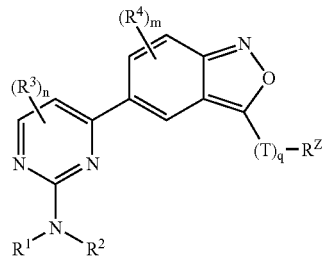

II-A

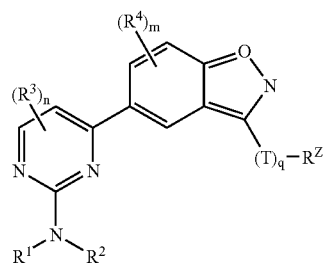

II-B wherein R$^1$, R$^2$, R$^3$, R$^4$, T, q, and R$^Z$ are as defined above and herein, and n is 0, 1 or 2, and m is 0, 1, 2 or 3.

In certain other exemplary embodiments, for compounds of general formulas II-A or II-B, R$^Z$ is Cy, and Cy is an optionally substituted 2-pyridyl, 3-pyridyl, 4-pyridyl, 4-pyrimidinyl, 5-pyrimidinyl, or tetrahydrofuranyl group and compounds have one of the general formulas:

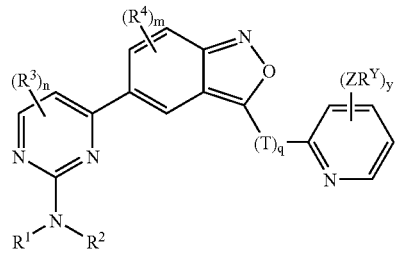

III-A

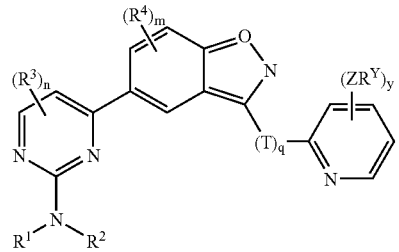

III-B

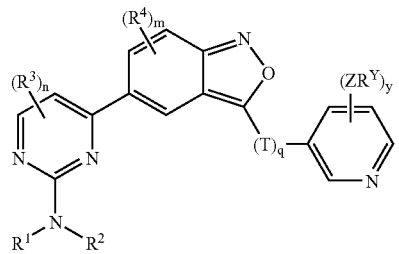

IV-A

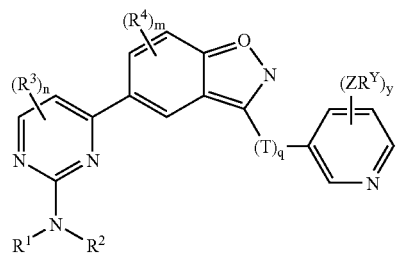

IV-B

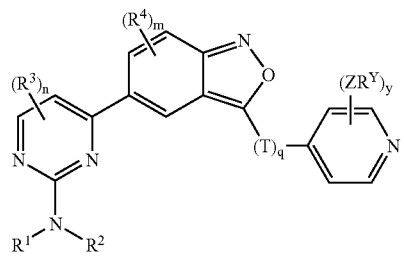

V-A

-continued
V-B
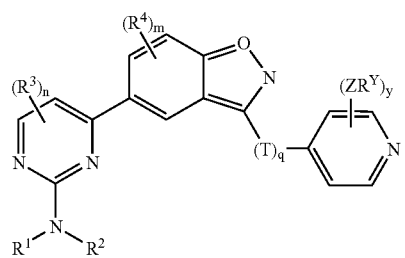
VI-A
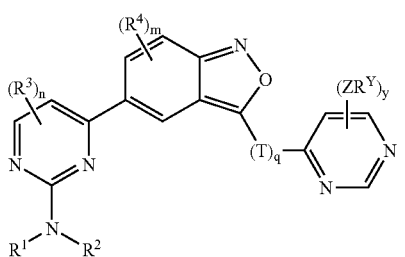
VI-B
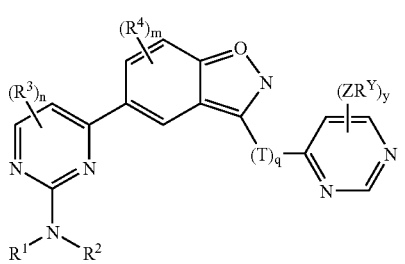
VII-A
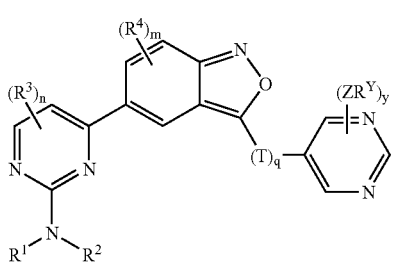
VII-B
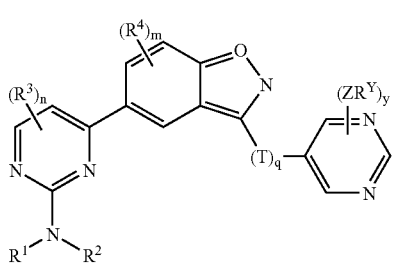
VIII-A
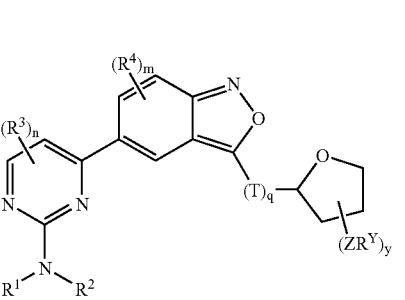
-continued
VIII-B
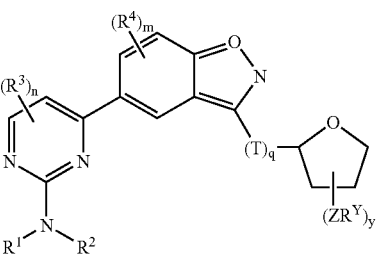
In certain preferred embodiments, for each of the subclasses of compounds described above and herein,
a) $R^2$ is hydrogen; $R^1$ is $(U)_p$—$R^5$, wherein p is 0, or p is 1 and U is selected from —$CH_2$—, —$CH_2CH_2$—, —$CH_2CH_2CH_2$—, —$CH_2CH_2CH_2CH_2$—, —$CO(CH_2)_{0-2}$—, —$CO(CH_2)_{0-2}O$—$CONH(CH_2)_{0-2}$—, or —$CO(CH_2)_{0-2}NH$—; and $R^5$ is any one of:
a-i
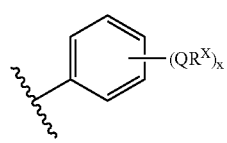
b-i
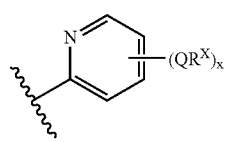
c-i
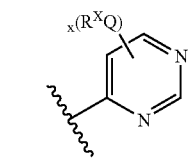
d-i
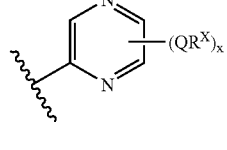
e-i
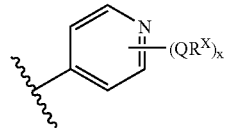
f-i
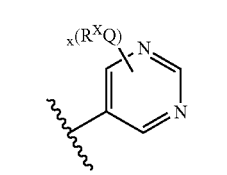
g-i
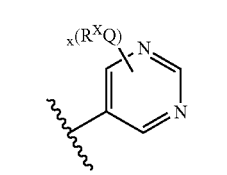

-continued

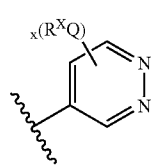

h-i b) n is 0, 1, or 2, and each occurrence of $R^3$ is selected from hydrogen or a $C_{1-4}$ alkyl group;

c) m is 0, 1, 2, or 3, and each occurrence of $R^4$ is selected from hydrogen, halo, $O(C_{1-4}$ alkyl), or a $C_{1-4}$ alkyl group;

d) q is 0, or q is 1 and T groups, when present, are selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and e) x is 0, 1, or 2, and y is 0, 1, or 2, and each occurrence of $QR^X$ and $ZR^Y$ is independently Cl, Br, F, CN, COOH, —N(CH$_3$)$_2$, —OH, CH$_2$OH, SO$_2$NH$_2$, or an optionally substituted group selected from $C_{1-4}$alkoxy, phenyl, phenyloxy, benzyl, or benzyloxy.

In certain preferred embodiments, for each of the subclasses of compounds described above and herein, a) $R^2$ is hydrogen, and $R^1$ is $(U)_p$—$R^5$, wherein p is 0, or p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and $R^5$ is a-i, b-i, e-i, or f-i;

b) n is 0, 1, or 2, and each occurrence of $R^3$ is selected from hydrogen or a $C_{1-4}$ alkyl group;

c) m is 0, 1, 2, or 3, and each occurrence of $R^4$ is selected from hydrogen, halo, $O(C_{1-4}$ alkyl), or a $C_{1-4}$ alkyl group;

d) q is 0, or q is 1 and T groups, when present, are selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and e) x is 0, 1, or 2, and y is 0, 1, or 2, and each occurrence of $QR^X$ and $ZR^Y$ is independently Cl, Br, F, CN, COOH, —N(CH$_3$)$_2$, —OH, CH$_2$OH, SO$_2$NH$_2$, or an optionally substituted group selected from $C_{1-4}$alkoxy, phenyl, phenyloxy, benzyl, or benzyloxy.

In certain preferred embodiments, for each of the subclasses of compounds described above and herein, a) $R^2$ is hydrogen; $R^1$ is $(U)_p$—$R^5$, wherein $R^2$ is hydrogen; $R^1$ is $(U)_p$—$R^5$, wherein p is 0, or p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and $R^5$ is a-i;

b) n is 0, 1, or 2, and each occurrence of $R^3$ is selected from hydrogen or a $C_{1-4}$ alkyl group;

c) m is 0, 1, 2, or 3, and each occurrence of $R^4$ is selected from hydrogen, halo, $O(C_{1-4}$ alkyl), or a $C_{1-4}$ alkyl group;

d) q is 0, or q is 1 and T groups, when present, are selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, CONH(CH$_2$)$_{0-2}$—, or —CO(CH$_2$)$_{0-2}$NH—; and e) x is 0, 1, or 2, and y is 0, 1, or 2, and each occurrence of $QR^X$ and $ZR^Y$ is independently Cl, Br, F, CN, COOH, —N(CH$_3$)$_2$, —OH, CH$_2$OH, SO$_2$NH$_2$, or an optionally substituted group selected from $C_{1-4}$alkoxy, phenyloxy, benzyl, or benzyloxy.

In certain other preferred embodiments, compounds have one of formulas II-A or II-B:

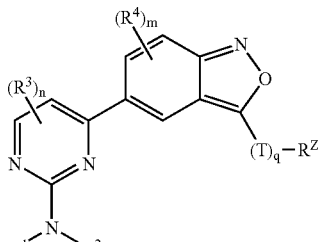

II-A

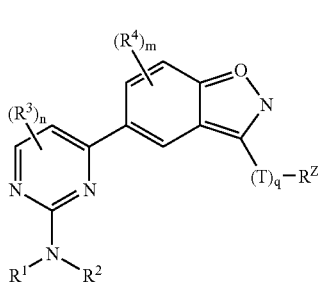

II-B a) wherein $R^Z$ is Cy, and Cy is any one of b-ii, c-ii, d-ii, e-ii, f-ii, g-ii, h-ii, i-ii, j-ii, k-ii, l-ii, m-ii, n-ii, o-ii, p-ii, q-ii, r-ii, s-ii, t-ii, u-ii, v-ii, x-ii, y-ii, z-ii, aa-ii, bb-ii, cc-ii, dd-ii, ee-ii, ff-ii, gg-ii, hh-ii, ii-ii, jj-ii, kk-ii, ll-ii, mm-ii, nn-ii, oo-ii, pp-ii, qq-ii, or rr-ii;

b) $R^2$ is hydrogen; $R^1$ is $(U)_p$—R5, wherein p is 0, or p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$, —CO(CH$_2$)$_{0-2}$O—, —CONH(CH$_2$)$_{0-2}$—, or —CO(CH$_2$)$_{0-2}$NH—; and $R^5$is any one of:

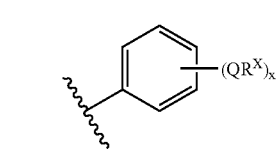

a-i

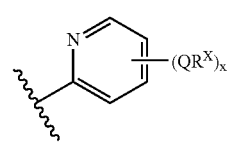

b-i

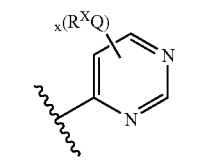

c-i

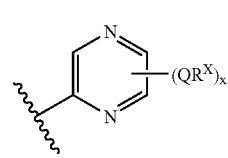

d-i

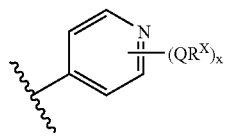

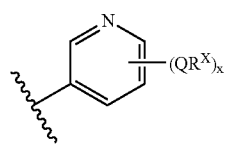

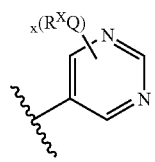

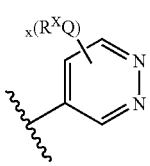

c) n is 0, 1, or 2, and each occurrence of $R^3$ is selected from hydrogen or a $C_{1-4}$ alkyl group;

d) m is 0, 1, 2, or 3, and each occurrence of $R^4$ is selected from hydrogen, halo, $O(C_{1-4}$ alkyl), or a $C_{1-4}$ alkyl group;

e) q is 0, or q is 1 and T groups, when present, are selected from —$CH_2$—, —$CH_2CH_2$—, —$CH_2CH_2CH_2$—, —$CH_2CH_2CH_2CH_2$—, —$CO(CH_2)_{0-2}$—, —$CO(CH_2)_{0-2}O$—, —$CONH(CH_2)_{0-2}$—, or —$CO(CH_2)_{0-2}NH$—; and f) x is 0, 1, or 2, and y is 0, 1, or 2, and each occurrence of $QR^X$ and $ZR^Y$ is independently Cl, Br, F, CN, COOH, —$N(CH_3)_2$, —OH, $CH_2OH$, $SO_2NH_2$, or an optionally substituted group selected from $C_{1-4}$alkoxy, phenyl, phenyloxy, benzyl, or benzyloxy.

In still other preferred embodiments, compounds have one of formulas II-A or II-B:

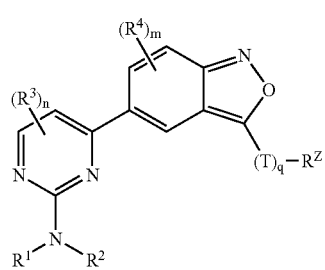

II-A

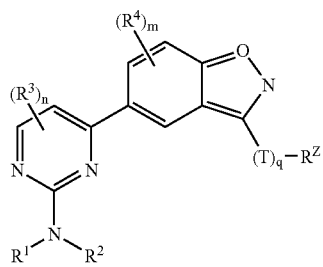

II-B a) wherein $R^Z$ is Cy, and Cy is any one of i-ii, j-ii, k-ii, l-ii, m-ii, n-ii, o-ii, p-ii, q-ii, r-ii, s-ii, t-ii, u-ii, v-ii, x-ii, y-ii, z-il, aa-ii, bb-ii, cc-ii, dd-ii, ee-ii, ff-ii, gg-ii, hh-ii, ii-ii, jj-ii, kk-ii, ll-ii, mm-ii, nn-ii, oo-ii, pp-ii, qq-ii, or rr-ii;

b) $R^2$ is hydrogen; $R^1$ is $(U)_p$—$R^5$, wherein p is 0, or p is 1 and U is selected from —$CH_2$—, —$CH_2CH_2$—, —$CH_2CH_2CH_2$—, —$CH_2CH_2CH_2CH_2$—, —$CO(CH_2)_{0-2}$—, —$CO(CH_2)_{0-2}O$—, —$CONH(CH_2)_{0-2}$—, or —$CO(CH_2)_{0-2}NH$—; and $R^5$ is any one of:

a-i

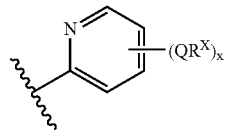

b-i

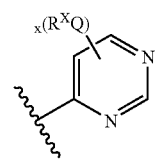

c-i

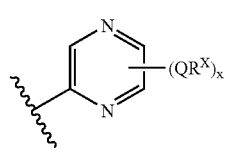

d-i

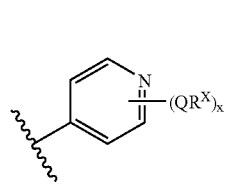

e-i

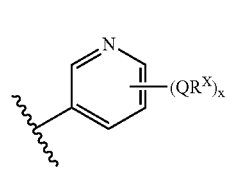

f-i

-continued

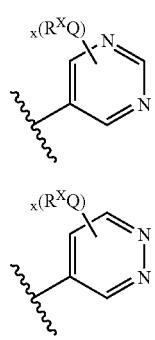

g-i h-i c) n is 0, 1, or 2, and each occurrence of R³ is selected from hydrogen or a $C_{1-4}$ alkyl group;

d) m is 0, 1, 2, or 3, and each occurrence of R⁴ is selected from hydrogen, halo, $O(C_{1-4}$ alkyl), or a $C_{1-4}$ alkyl group;

e) q is 0, or q is 1 and T groups, when present, are selected from —CH₂—, —CH₂CH₂—, —CH₂CH₂CH₂—, —CH₂CH₂CH₂CH₂—, —CO(CH₂)₀₋₂—, —CO(CH₂)₀₋₂O—, CONH(CH₂)₀₋₂—, or —CO(CH₂)₀₋₂NH—; and f) x is 0, 1, or 2, and y is 0, 1, or 2, and each occurrence of QR^X and ZR^Y is independently Cl, Br, F, CN, COOH, —N(CH₃)₂, —OH, CH₂OH, SO₂NH₂, or an optionally substituted group selected from $C_{1-4}$alkoxy, phenyl, phenyloxy, benzyl, or benzyloxy.

Representative examples of compounds of formula I are set forth below in Table 1.

TABLE 1

Examples of Compounds of Formula I:

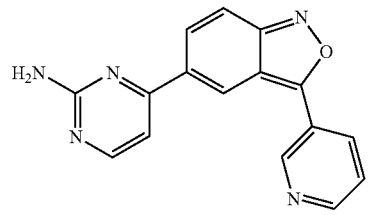

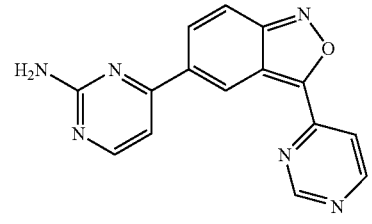

I-3
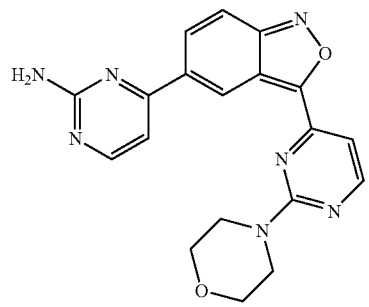

-continued

I-4
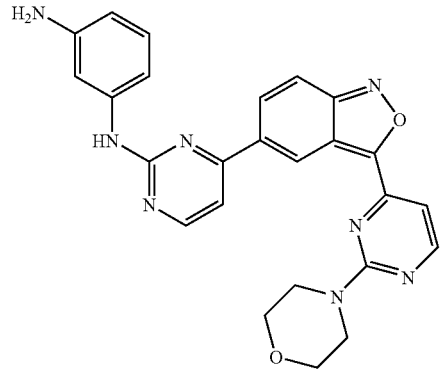

I-5
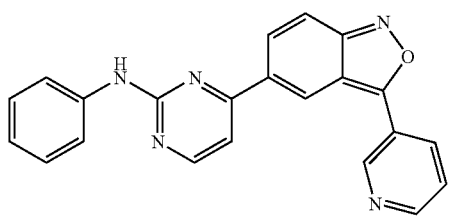

I-6
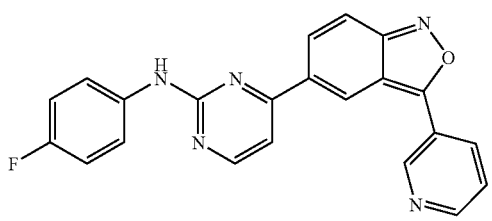

I-7
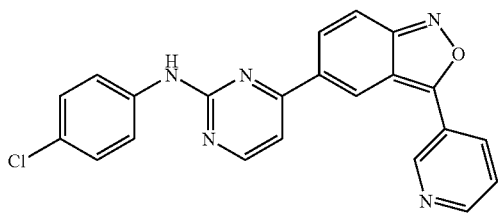

I-8
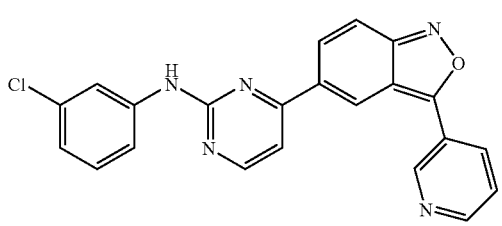

I-9
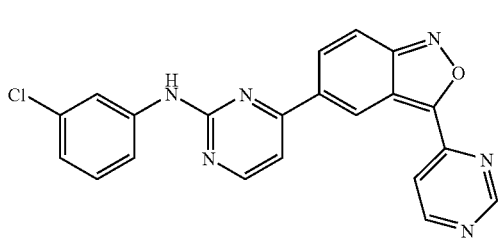

-continued
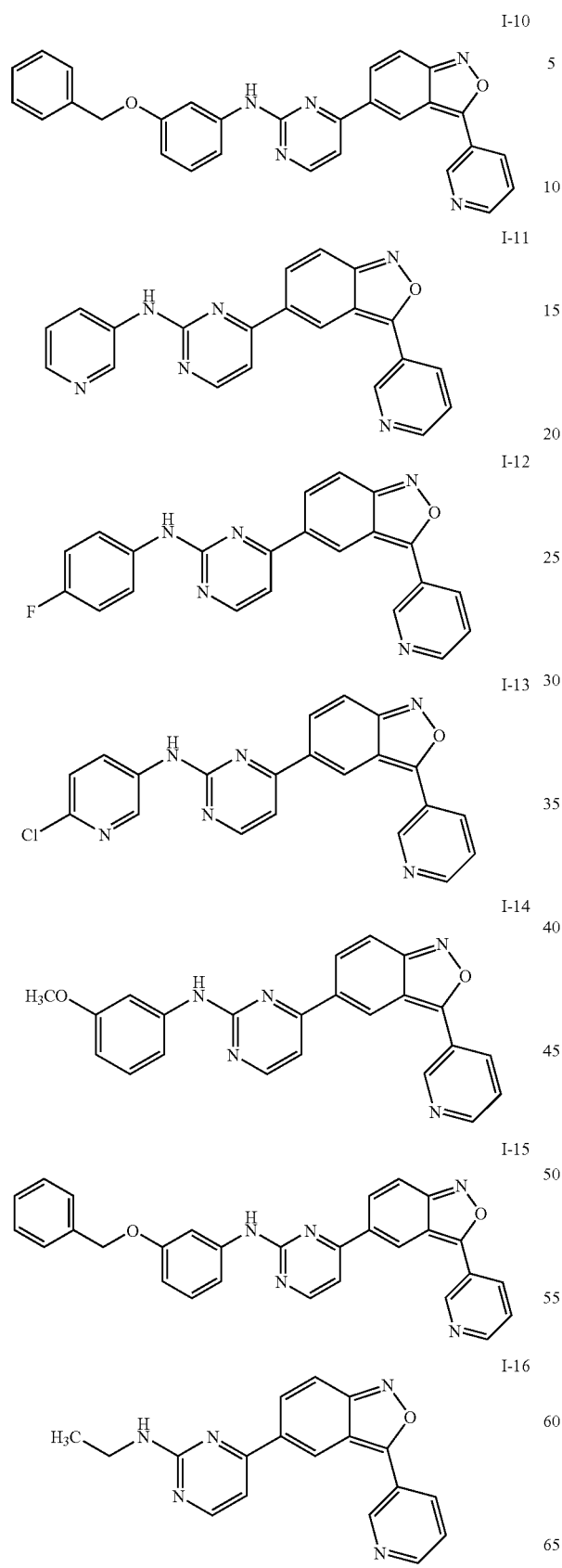
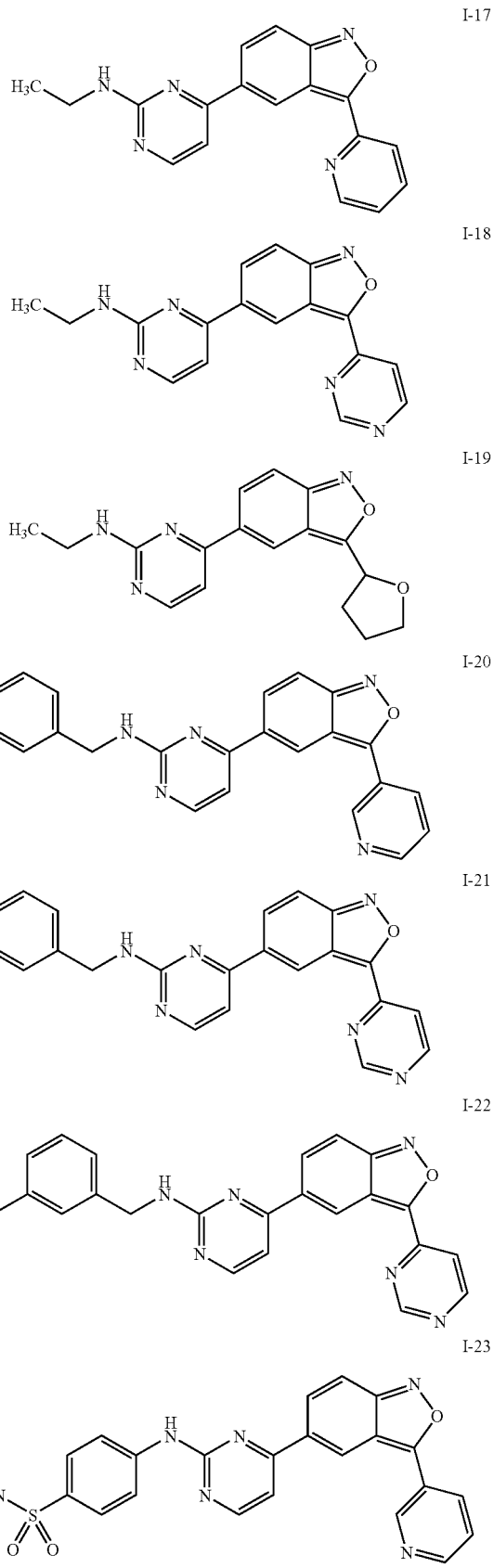

I-24
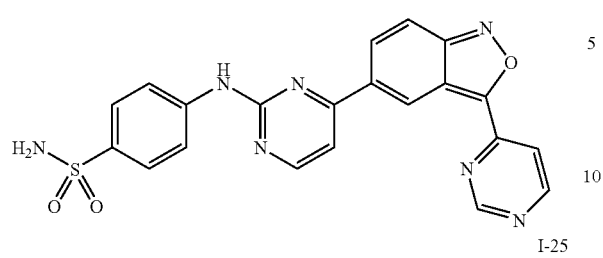
I-25
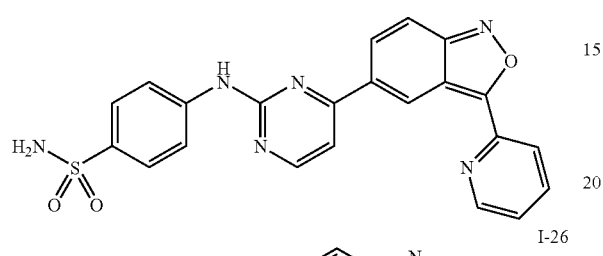
I-26
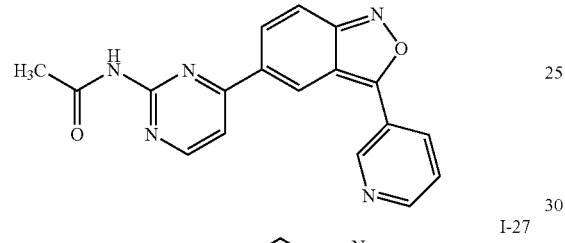
I-27
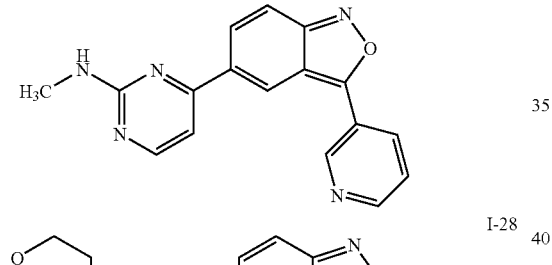
I-28
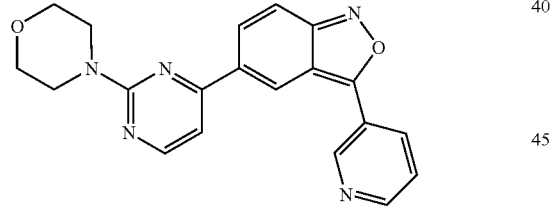
I-29
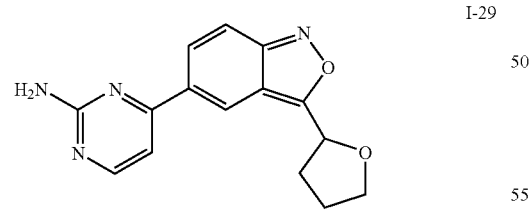
I-30
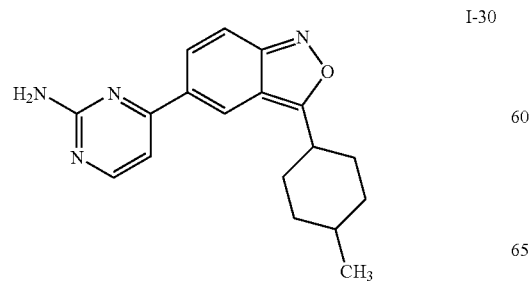
I-31
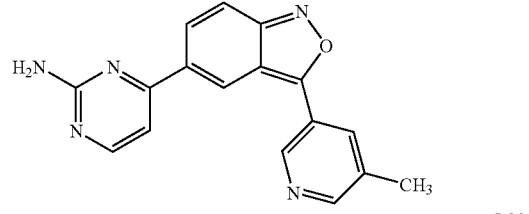
I-32
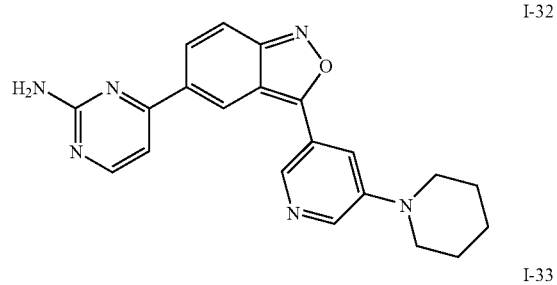
I-33
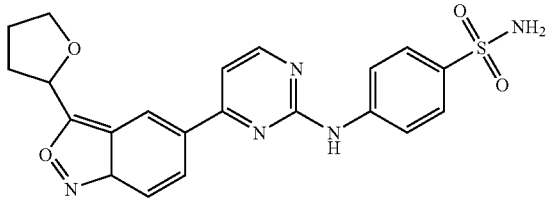
I-34
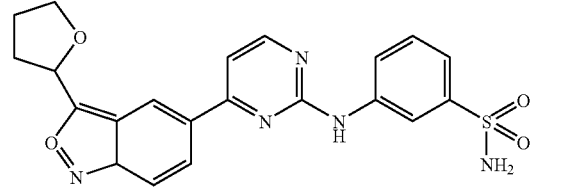
I-35
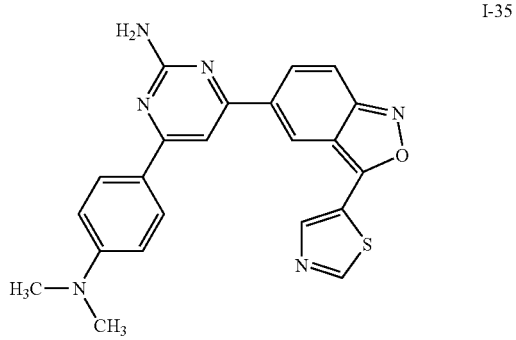
I-36

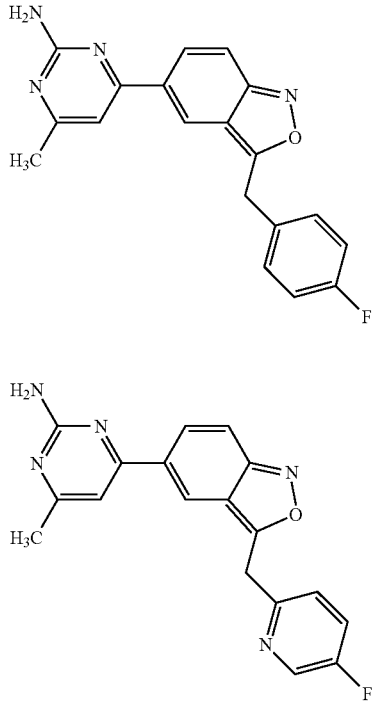

4. General Synthetic Methodology:

The compounds of this invention may be prepared in general by methods known to those skilled in the art for analogous compounds, as illustrated by the general scheme below, and the preparative examples that follow.

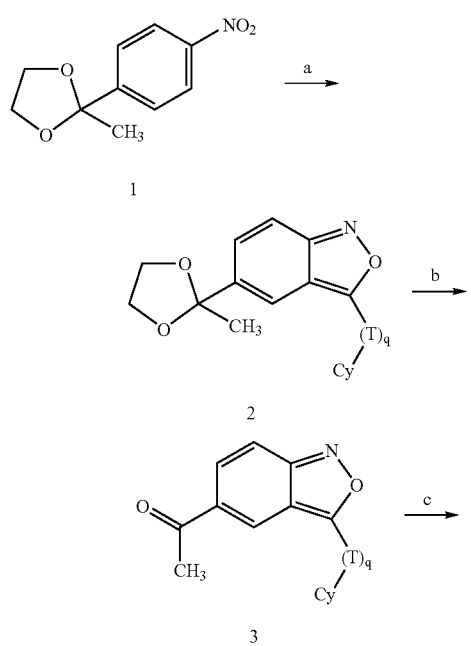

Reagents and Conditions: (a) ArCH$_2$CN, KOH, MeOH, Room Temperature (rt); (b) Formic Acid, rt (c) N,N-dimethylformamide dimethyl acetal, CH$_3$CN, 80° C.; (d) N-phenylguanidine-HCl, CH$_3$CN, reflux.

Scheme I above shows a synthetic route for preparing certain exemplary compounds of the present invention when R$^Z$ is Cy. For various (T)$_q$-Cy groups, the intermediate 3 can be obtained commercially or obtained by known methods as shown in steps (a) and (b) above. See R. B. Davis and L. C. Pizzini, *J. Org. Chem.*, 1960, 25, 1884–1888. A Mannich reaction provides intermediate 4, which can be treated with phenylguanidine to give the desired compounds 5. It will be obvious to one skilled in the art that phenylguanidine may be replaced with other arylguanidines, which are readily available, to provide other compounds of this invention.

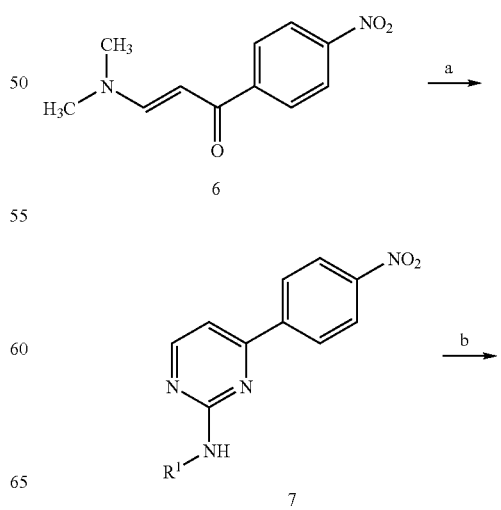

-continued

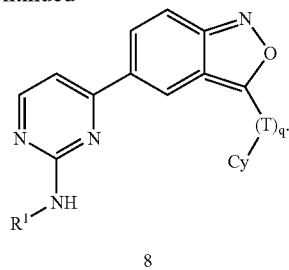

8

Reagents and Conditions: (a) R$^1$NHC(=NH)NH$_2$—HCl, CH$_3$CN, Reflux; (b) Cy-(T)$_q$—CH$_2$CN, KOH, MeOH, Room Temperature (rt); (c) R$^4$B(OH)$_2$, Pd(PPh$_3$)$_4$, Na$_2$CO$_3$, dioxane Scheme II above shows an alternative synthetic route where the pyrimidine ring is constructed before the benzisoxazole ring. Steps (a) and (b) are analogous to the corresponding steps shown above in Scheme I except that they are performed in the opposite order.

Scheme III

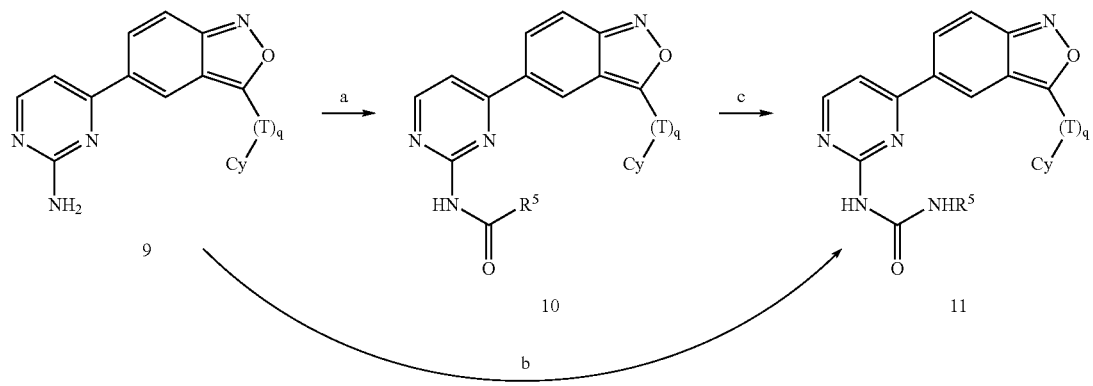

Reagents and conditions: (a) NaH, DMF/THF 1:1, R$^5$C(O)Cl, ambient temp; wherein R$^1$ is —C(O)R$^5$; (b) R$^5$NCO, DMSO, ambient temp/80° C.; wherein R$^1$ is —C(O)NHR$^5$; (c) [from the p-NO$_2$-phenyl carbamic esters] R$^5$NH$_2$, DMSO/THF 1:1, 80° C.; wherein R$^1$ is —C(O)NHR$^5$.

Alternatively, reagents and conditions for carbamate formation (not shown): (a) R$^5$OC(O)Cl, DMSO, DIPEA, ambient temp; wherein R$^1$ is —C(O)OR$^5$.

Scheme III shows general methods for the preparation of compounds of Formula I wherein NH—R$^1$ taken together form an amide (shown in step (a) above), carbamate (not shown) or a urea (shown in steps (a) and (c) or step (b) above). Acylation of the aminopyrimidine with acid chlorides, chloroformates and isocyanates provides amides, cabamates and ureas respectively. Alternatively, ureas can be generated by a nucleophilic displacement reaction with a primary or secondary amine via the corresponding p-nitrophenylcarbamate.

Scheme IV

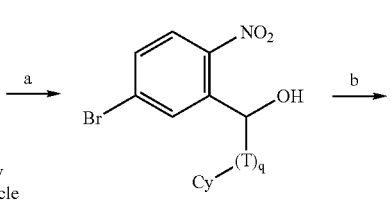

X = Br or I
Cy is an optionally substituted heterocycle or heteroaryl

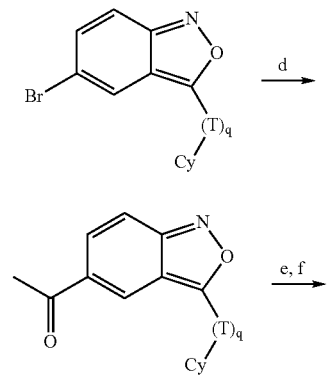

-continued

-continued

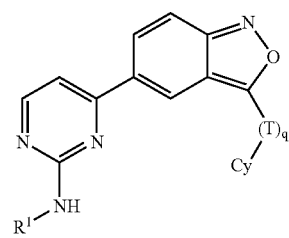

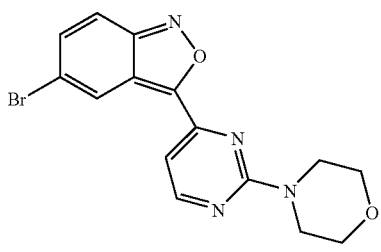

(a) i: nBuLi or iPrMgCl, THF ii: 5-bromo-2-nitrobenzaldehyde (b) MnO₂ or Dess-Martin (c) SnCl₂, HOAc—H₂O (d) i: PdCl₂(PPh₃)₄, tributyl(1-ethoxyvinyl) tin, toluene, 100° C. ii: conc HCl (e) DMF-DMA, 100° C. (f) guanidine, K₂CO₃, DMF, 100° C.

Scheme IV above depicts a general method for the preparation of compounds of general formula I, most preferably compounds where Cy is a heterocyclyl or heteroaryl group. Scheme V below depicts one exemplary embodiment where q is 0 and Cy is optionally substituted pyrimidine.

Scheme V

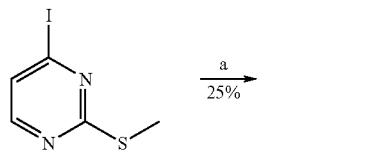

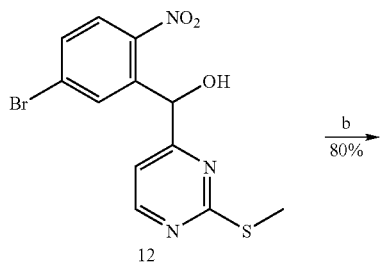

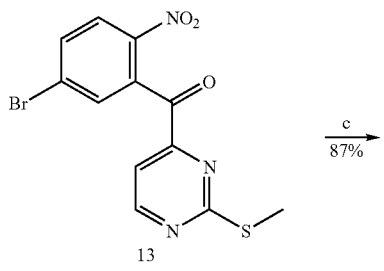

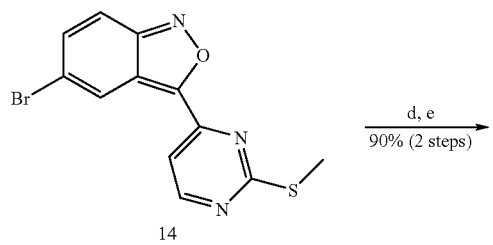

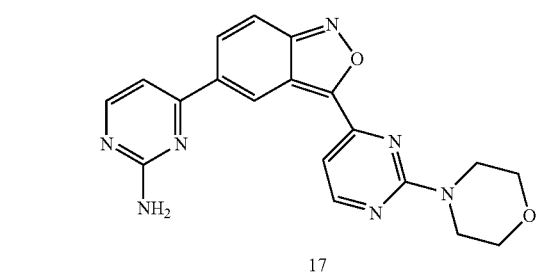

(a) i: iPrMgCl, THF/DCM 0° C. ii: 5-bromo-2-nitrobenzaldehyde (b) MnO₂ (c) SnCl₂, HOAc—H₂O (d) mCPBA, DCM (e) morpholine, DMSO, 70° C. (f) i: PdCl₂(PPh₃)₄, tributyl(1ethoxyvinyl) tin, toluene, 100° C. ii: conc HCl (g) DMF-DMA, 100° C. (h) guanidine, K₂CO₃, DMF, 100° C.

Scheme VI below depicts a general method for the preparation of compounds of general formula I, where T and q are as defined generally above, and $R^Z$ is preferably R, CN or Cy.

Scheme VI

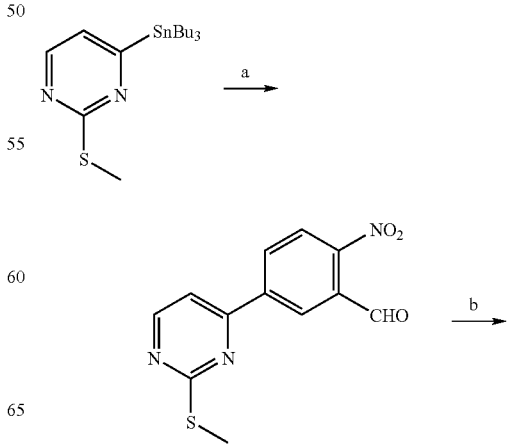

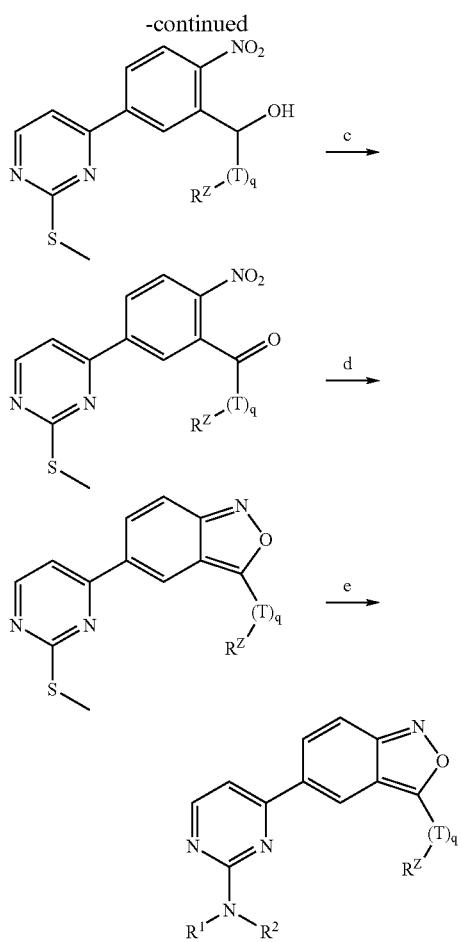

(a) PdCl$_2$(PPh$_3$)$_4$, -bromo-2-nitrobenzaldehydel, toluene, 100° C. (b) R$^Z$-(T)$_q$—MgBr, CeCl$_3$, THF, −78->0° C. (c) MnO$_2$ or Dess-Martin (d) SnCl$_2$, HOAc—H$_2$O (e) Oxone or m-CPBA (f) HNR$^1$R$^2$, DMSO, 70° C.

Although certain exemplary embodiments are depicted and described above and herein, it will be appreciated that a compounds of the invention can be prepared according to the methods described generally above using appropriate starting materials.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In preferred embodiments, the compounds are useful for the treatment of allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia (e.g., stroke), baldness, cancer, hepatomegaly, cardiovascular disease including cardiomegaly, cystic fibrosis, viral disease, autoimmune diseases, atherosclerosis, restenosis, psoriasis, inflammation, hypertension, angina pectoris, cerebrovascular contraction, peripheral circulation disorder, premature birth, arteriosclerosis, vasospasm (cerebral vasospasm, coronary vasospasm), retinopathy, erectile dysfunction (ED), AIDS, osteoporosis, Crohn's Disease and colitis, neurite outgrowth, and Raynaud's Disease. In preferred embodiments, the disease, condition, or disorder is atherosclerosis, hypertension, erectile dysfunction (ED), reperfusion/ischemia (e.g., stroke), or vasospasm (cerebral vasospasm and coronary vasospasm).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a GSK-3, JAK-3, FLT-3, PIM-1, SYK, or PDK-1.

Pharmaceutically acceptable salts are well known in the art. For example, S. M. Berge et al., describe pharmaceutically acceptable salts in detail in *J. Pharmaceutical Sciences*, 1977, 66, 1–19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formnate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar--agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice,. additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of GSK-3, JAK-3, FLT-3, PIM-1, SYK, or PDK-1, and thus, without wishing to be bound by any particular theory, the compounds and compositions are particularly useful for treating or lessening the severity of a disease, condition, or disorder where activation of one or more of GSK-3, JAK-3, FLT-3, PIM-1, SYK, or PDK-1 is implicated in the disease, condition, or disorder. When activation of GSK-3, JAK-3, FLT-3, PIM-1, SYK, or PDK-1 is implicated in a particular disease, condition, or disorder, the disease, condition, or disorder may also be referred to as "GSK-3, JAK-3, FLT-3, PIM-1, SYK, or PDK-1-mediated disease" or disease symptom. Accordingly, in another aspect, the present invention provides a method for treating or lessening the severity of a disease, condition, or disorder where activation or one or more of GSK-3, JAK-3, FLT-3, PIM-1, SYK, or PDK-1 is implicated in the disease state.

The activity of a compound utilized in this invention as an inhibitor of GSK-3, JAK-3, FLT-3, PIM-1, SYK, or PDK-1, may be assayed in vitro, in vivo or in a cell line. In vitro assays include assays that determine inhibition of either the phosphorylation activity or ATPase activity of activated GSK-3, JAK-3, FLT-3, PIM-1, SYK, or PDK-1. Alternate in vitro assays quantitate the ability of the inhibitor to bind to GSK-3, JAK-3, FLT-3, PIM-1, SYK, or PDK-1. Inhibitor binding may be measured by radiolabelling the inhibitor prior to binding, isolating the inhibitor/GSK-3, JAK-3, FLT-3, PIM-1, SYK, or PDK-1 complex and determining the amount of radiolabel bound. Alternatively, inhibitor binding may be determined by running a competition experiment where new inhibitors are incubated with GSK-3, JAK-3, FLT-3, PIM-1, SYK, or PDK-1 bound to known radioligands.

The term "measurably inhibit", as used herein means a measurable change in GSK-3, JAK-3, FLT-3, PIM-1, SYK, or PDK-1 activity between a sample comprising said composition and a GSK-3, JAK-3, FLT-3, PIM-1, SYK, or PDK-1 kinase and an equivalent sample comprising GSK-3, JAK-3, FLT-3, PIM-1, SYK, or PDK-1 kinase in the absence of said composition.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases (e.g., Alzheimer's disease, Huntington's disease, Parkinson's disease and basal ganglia movement disorders, chorea, dystonia, Wilson Disease, Pick Disease, frontal lobe degeneration, progessive supranuclear palsy (PSP), Creutzfeldt-Jakob Disease, taupathology and corticobasal degeneration (CBD)), psychotic disorders (e.g., schizophrenia, AIDS-associated dementia, depression, bipolar disorder, and anxiety disorders), cardiovascular diseases, allergy, asthma, diabetes, amyotrophic lateral sclerosis (AML, Lou Gehrig's disease), multiple sclerosis (MS), cardiomyocyte hypertrophy, reperfusion/ischemia, stroke, and baldness.

The term "JAK-mediated disease", as used herein means any disease or other deleterious condition in which a JAK family kinase, in particular JAK-3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. PDK1-mediated diseases or conditions include, but are not limited to, proliferative disorders, and cancer. Preferably, said cancer is selected from pancreatic, prostate, or ovarian cancer.

The term "FLT-3-mediated disease", as used herein means any disease or other deleterious condition in which a FLT-3 family kinase is known to play a role. Such conditions include, without limitation, hematopoietic disorders, in particular, acute-myelogenous leukemia (AML), acute-promyelocytic leukemia (APL), and acute lymphocytic leukemia (ALL).

The term "c-KIT-mediated disease", as used herein means any disease or other deleterious condition in which a c-KIT family kinase is known to play a role. Such conditions include, without limitation, AML, chronic myelogenous leukemia (CML), mastocytosis, anaplastic large-cell lymphoma, ALL, gastrointestinal stromal tumor (GIST), T-cell lymphoma, adenoid cytsic carcinoma, angiosarcoma, endometrial carcinoma, small cell lung carcinoma, prostate cancer, ovarian cancer, breast carcinoma, thyroid carcinoma, malignant melanoma and colon carcinoma.

The term "PIM-1-mediated disease", as used herein means any disease or other deleterious condition in which a PIM-1 family kinase is known to play a role. Such conditions include, without limitation, cancer, particularly lymphomas, inflammatory disease, including asthma, allergy, and Crohn disease, and immunosuppression, including transplantation rejection and autoimmune disease.

The term "SYK-mediated disease" or "SYK-mediated condition", as used herein, means any disease or other deleterious condition in which SYK protein kinase is known to play a role. Such conditions include, without limitation, allergic disorders, especially asthma.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon® ; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting GSK-3, JAK-3, FLT-3, PIM-1, SYK, or PDK-1 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of GSK-3, JAK-3, FLT-3, PIM-1, SYK, or PDK-1 kinase activity in a biological sample is useful for a variety of purposes that are known to one of skill in the art. Examples of such purposes include, but are not limited to, blood transfusion, organ-transplantation, biological specimen storage, and biological assays.

In order that the invention described herein may be more fully understood, the following examples are set forth. It should be understood that these examples are for illustrative purposes only and are not to be construed as limiting this invention in any manner.

EXAMPLES

Example 1

Synthesis of Exemplary Compounds of the Invention

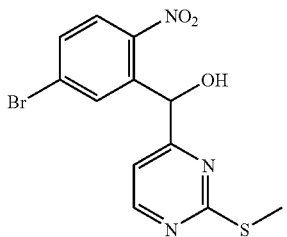

1: To a stirred solution of 4-iodo-2-methylthiopyrimidine (683 mg, 2.71 mMol) in $CH_2Cl_2$ at 0° C. was added iPrMgCl (1.62 mL, 3.25 mMol, 2.0 M in THF). After 25 min at 0° C., the solution was warmed to ambient temperature for 5 min. and re-cooled to 0° C. Then, a solution of 5-bromo-2-nitrobenzaldehyde (624 mg, 2.71 mMol) in $CH_2Cl_2$ (5 mL) was added dropwise and the solution was stirred at 0° C. for 1 h. The reaction was warmed to ambient temperature and poured into saturated $NH_4Cl$. The mixture was extracted with several portions of $CH_2Cl_2$, washed with brine, dried ($MgSO_4$), filtered and concentrated. Flash chromatography (17% EtOAc-hexanes) provided 245 mg (0.688 mMol, 25% yield) of the desired product (1). FIA (M+H$^+$) 355.9

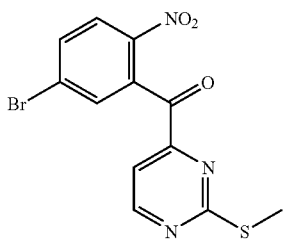

2: To a solution of 1 (245 mg, 0.688 mMol) in $CHCl_3$ (5 mL) at ambient temperature was added activated $MnO_2 \cdot 2H_2O$ (1.0 g). The mixture was stirred for 1 h., filtered and concentrated to provide 2 (194 mg, 0.548 mMol, 80% yield) as a yellow solid.

$^1$H NMR (CDCl$_3$, 500 MHz) δ 8.80 (d, 1H), 8.08 (d, 1H), 7.84 (dd, 1H), 7.74 (d, 1H), 7.71 (d, 1H), 2.27 (s, 3H) ppm.

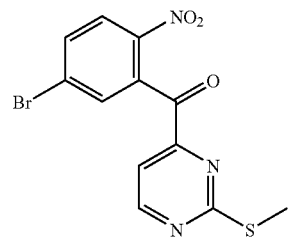

3: A stirred mixture of 2 (190 mg, 0.536 mMol) in HOAc:EtOH:H$_2$O (5 mL, 2:1:2) was treated with $SnCl_2 \cdot 2H_2O$ (360 mg, 1.6 mMol) at ambient temperature for 3.5 h. The mixture was poured into water and EtOAc was added. The pH was adjusted to 14 with 6 N NaOH (aq.) under vigorous stirring. The layers were separated and the aqueous layer was extracted with EtOAc. The oragnic phase was washed with brine, dried (MgSO$_4$), filtered through a thin bed of SiO$_2$ and concentrated. HPLC and FHA indicated a 50/50 mixture of 2 and 3. The crude material was re-subjected to the reaction conditions for 16 h. The reaction was worked up as described above to provide 3 (150 mg, 0.466 mMol, 87% yield) as a yellow solid.

FIA (M+H$^+$) 321.8; HPLC t$_r$=8.55 min.; $^1$H NMR (CDCl$_3$, 500 MHz) δ 8.72 (d, 1H), 8.57 (dd, 1H), 7.68 (d, 1H), 7.60 (d, 1H), 7.45 (dd, 1H), 2.75 (s, 3H) ppm.

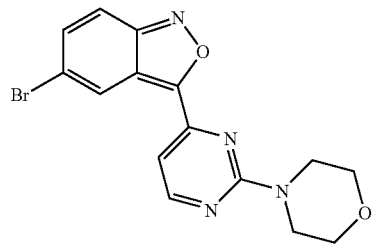

4: A stirred solution of 3 (150 mg, 0.466 mMol) in CH$_2$Cl$_2$ was treated with m-chloroperbenzoic acid (225 mg, 1.0 mMoL) at ambient temperature for 35 min. The reaction mixture was diluted with , washed with dilute aqueous sodium bisulfite and NaHCO$_3$. The organic phase was dried (MgSO$_4$), filtered and concentrated to provide a mixture of the sulfone and sulfoxide. This material was used directly in the next step with any attempt at purification or separation of the components.

FIA (M+H$^+$) 337.9 and 353.9; HPLC t$_r$=5.13 and 5.99 min.

The above mixture in DMSO (3 mL) was treated with morpholine (0.12 mL, 1.4 mMol) at 70° C. for 35 min. The resulting slurry was cooled to ambient temperature and poured into water and the solid was collected by filtration. The mother liquid was extracted with EtOAc and the organic phase was washed with brine. The solid and the organic phase were combined, concentrated, diluted with toluene and concentrated again to provide 4 (151 mg, 0.418 mMol, 90% yield) as a yellow solid.

FIA (M+H$^+$) 361.0; HPLC t$_r$=8.18 min.

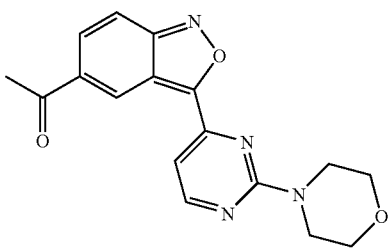

5: To a solution of 4 (151 mg, 0.418 mMol) and PdCl$_2$(PPh$_3$)$_2$ in dry degassed toluene at 80° C. was added dropwise tributyl(1-ethoxyvinyl) tin (0.28 mL, 0.84 mMol) over 60 min. The reaction was cooled to ambient temperature and 6N HCl (5 mL) was added. After 30 min of vigorous stirring, the mixture was washed with Et$_2$O, the pH of the organic phase was adjusted to 14 with 6N NaOH, and the mixture was extracted with several portions of EtOAc. The combined organic phases were washed with brine, dried (MgSO$_4$), filtered and concentrated to provide a yellow solid. The solid was washed with several small portions of EtOAc. To provide 5 (72 mg). The mother liquor was then treated with wet TFA for 30 min. The pH of the organic phase was adjusted to 14 with 6N NaOH, and the mixture was extracted with several portions of EtOAc. The organic layer was washed with brine, dried (MgSO$_4$), filtered and concentrated. The resulting material was subjected to flash chromatography to provide additional 5 (80 mg, 0.24 mMol, 59% yield).

FIA (M+H$^+$) 325.1; HPLC $t_r$=6.77 min.

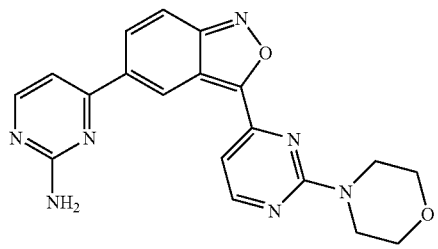

6: A mixture of 5 (80 mg, 0.24 mMol) in DMFDMA (2 mL) was heated to 100° C. for 3 h. Then, CH$_3$CN was added and heating was continued at 90° C. for 4 h. The mixture was concentrated to provide an orange solid (65 mg, 0.17 mMol) that was collected by filtration and rinsed with a small amount of DMFDMA.

FIA (M+H$^+$) 380.2; HPLC $t_r$=5.77 min.

A mixture of 20.7 mg (0.055 mMol) of the above solid, powdered K$_2$CO$_3$ (38 mg, 0.275 mMol) and guanindine hydrochloride (8.0 mg, 0.082 mMol) in DMF (0.5 mL) was heated to 100° C. for 5 h during which time a thick slurry forms. The mixture was cooled, H$_2$O was added and the remaining solid was collected by filtration and washed with additional H$_2$O and dried under vacuum to provide 6 (19.7 mg) as a yellow solid.

Bis-TFA salt: The solid was treated with an excess of TFA for approximately 15 min. in a mixture of MeOH and Cl$_2$CH$_2$ (~1:1). The solution was concentrated and the volatile components were removed under vacuum to provide 6 (32.8 mg, 0.054 mMol, 98% yield) as a yellow solid.

FIA (M+H$^+$) 376.2; HPLC $t_r$=6.77 min.; $^1$H NMR (DMSO, 500 MHz) δ 9.00 (s, 1H), 8.71 (d, 1H), 8.45 (d, 1H), 8.18 (d, 1H), 7.93 (d, 1H), 7.43 (d, 1H), 7.28 (d, 1H), 7.40–7.10 (br s, 2H), 3.88 (m, 4H), 3.78 (m, 4H) ppm.

Example 2

Inhibition of GSK-3;

Compounds were screened for their ability to inhibit GSK-3β(AA 1–420) activity using a standard coupled enzyme system (Fox et al. (1998) *Protein Sci.* 7, 2249). Reactions were carried out in a solution containing 100 mM HEPES (pH 7.5), 10 mM MgCl$_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The K$_i$ values were determined from the rate data as a function of inhibitor concentration.

Example 3

JAK Inhibition Assay

Compound inhibition of JAK was assayed by the method described by G. R. Brown, et al, *Bioorg. Med. Chem. Lett.* 2000, vol. 10, pp 575–579 in the following manner. Into Maxisorb plates, previously coated at 4° C. with Poly (Glu, Ala, Tyr) 6:3:1 then washed with phosphate buffered saline 0.05% and Tween (PBST), was added 2 μM ATP, 5 mM MgCl$_2$, and a solution of compound in DMSO. The reaction was started with JAK enzyme and the plates incubated for 60 minutes at 30° C. The plates were then washed with PBST, 100 μL HRP-Conjugated 4G10 antibody was added, and the plate incubated for 90 minutes at 30° C. The plate was again washed with PBST, 100 μL TMB solution is added, and the plates were incubated for another 30 minutes at 30° C. Sulfuric acid (100 μL of 1M) was added to stop the reaction and the plate is read at 450 nm to obtain the optical densities for analysis to determine IC$_{50}$ values and K$_i$ values. In certain embodiments, compounds I-1, I-3 and I-4 exhibit K$_i$ values less than 2.5 μM. In certain other embodiments, compounds I-1 and I-3 exhibit K$_i$ values less than 1.5 μM.

Example 4

FLT-3 Inhibition Assay

Compounds were screened for their ability to inhibit FLT-3 activity using a radiometric filter-binding assay. This assay monitors the $^{33}$P incorporation into a substrate poly (Glu, Tyr) 4:1 (pE4Y). Reactions were carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 90 µM ATP and 0.5 mg/mL pE4Y (both from Sigma Chemicals, St Louis, Mo.). The final concentration of compounds is generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH7.5), 10 mM MgCl$_2$, 25 mM NaCl, 1 mg/ml pE4Y and 180 µM ATP(containing 0.3 µCi of [γ-$^{33}$P] ATP for each reaction). Solution 2 contains 100 mM HEPES (pH7.5), 10 mM MgCl$_2$, 25 mM NaCl, 2 mM DTT, 0.02% BSA and 3 nM FLT-3. The assay was run on a 96 well plate by mixing 50 µL each of Solution1 and 2.5 mL of the test compounds. The reaction was initiated with Solution2. After incubation for 20 minutes at room temperature, the reaction was stopped with 50 µL of 20% TCA containing 0.4 mM of ATP. All of the reaction volume was then transferred to a filter plate and washed with 5% TCA by a Harvester9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an IC$_{50}$ or K$_i$.

Example 5

PDK-1 Inhibition Assay

Compounds were screened for their ability to inhibit PDK-1 using a radioactive-phosphate incorporation assay (Pitt and Lee, J. Biomol. Screen., (1996) 1, 47). Assays were carried out in a mixture of 100 mM HEPES (pH 7.5), 10 mM MgCl$_2$, 25 mM NaCl, 2 mM DTT. Final substrate concentrations in the assay were 40 µM ATP (Sigma Chemicals) and 65 µM peptide (PDKtide, Upstate, Lake Placid, N.Y.). Assays were carried out at 30° C. and 25 nM PDK-1 in the presence of ~27.5 nCi/µL of [γ-$^{32}$P]ATP (Amersham Pharmacia Biotech, Amersham, UK). An assay stock buffer solution was prepared containing all of the reagents listed above, with the exception of ATP, and the test compound of interest. 15 µl of the stock solution was placed in a 96 well plate followed by addition of 1 µl of 0.5 mM DMSO stock containing the test compound (final compound concentration 25 µM, final DMSO concentration 5%). The plate was preincubated for about 10 minutes at 30° C. and the reaction initiated by addition of 4 µl ATP (final concentration 40 µM).

The reaction was stopped after 10 minutes by the addition of 100 µL 100 mM phosphoric acid, 0.01% Tween-20. A phosphocellulose 96 well plate (Millipore, Cat no. MAPH-NOB50) was pretreated with 100 µL 100 mM phosphoric acid, 0.01% Tween-20 prior to the addition of the reaction mixture (100 µL). The spots were left to soak for at least 5 minutes, prior to wash steps (4×200 µL 100 mM phosphoric acid, 0.01% Tween-20). After drying, 20 µL Optiphase 'SuperMix' liquid scintillation cocktail (Perkin Elmer) was added to the well prior to scintillation counting (1450 Microbeta Liquid Scintillation Counter, Wallac).

Compounds showing greater than 50% inhibition versus standard wells containing the assay mixture and DMSO without test compound were titrated to determine IC$_{50}$ values.

Example 6

Inhibition of SYK

Compounds were screened for their ability to inhibit SYK using a standard coupled enzyme assay (Fox et al (1998) *Protein Sci* 7, 2249). Reactions were carried out in 100 mM HEPES pH 7.5, 10 mM MgCl2, 25 mM NaCl, 1 mM DTT and 1.5% DMSO. Final substrate concentrations in the assay were 200 µM ATP (Sigma chemical Co.) and 4 µM poly Gly-Tyr peptide (Sigma Chemical Co.). Assays were carried out at 30° C. and 200 nM SYK. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of SYK, DTT and the test compound of interest. 56 µl of the test reaction was placed in a 96 well plate followed by the addition of 1 µl of 2 mM DMSO stock containing the test compound (final compound concentration 30 µM). The plate was pre-incubated for ~10 minutes at 30° C. and the reaction initiated by the addition of 10 µl of enzyme (final concentration 25 nM). Rates of reaction were obtained using a BioRad Ultramark plate reader (Hercules, Calif.) over a 5 minute read time at 30° C., and K$_i$ values were determined according to standard methods.

What is claimed is:
1. A compound of formula (II)-A:

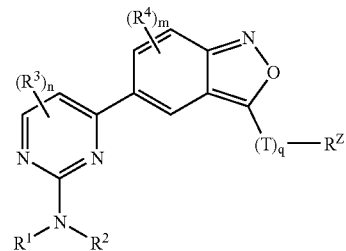

II-A or a pharmaceutically acceptable salt thereof, wherein:
R$^1$ and R$^2$ are each independently selected from hydrogen, or (U)$_p$—R$^5$, wherein p is 0 or 1, U is an optionally substituted C$_1$–C$_6$ alkylidene chain wherein up to two non-adjacent methylene units of U are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR, and R$^5$ is an optionally substituted group selected from optionally substituted C$_{1-10}$ aliphatic, an aryl group selected from a 5–6 membered monocyclic or an 8–10 membered bicyclic ring having 0–5 heteroatoms independently selected from nitrogen, oxygen, or sulfur; a 3-8-membered saturated or partially unsaturated monocyclic ring having 0–3 heteroatoms independently selected from nitrogen, oxygen, or sulfur, or an 8–10-membered saturated or partially unsaturated bicyclic ring system having 0–5 heteroatoms independently selected from nitrogen, oxygen, or sulfur; or R$^1$ and R$^2$ taken together with the nitrogen atom form an optionally substituted 5–8 membered heterocyclyl or heteroaryl ring having 1–3 heteroatoms independently selected from nitrogen, oxygen, or sulfur, wherein R$^1$ and R$^2$ are each independently optionally substituted with up to five substituents selected from Q–R$^X$; wherein Q is a bond or is an optionally substituted C$_1$–C$_6$ alkylidene chain wherein up to two non-adjacent methylene units of Q are optionally replaced by CO, CO$_2$, COCO, CONR, OCONR, NRNR, NRNRCO, NRCO, NRCO$_2$, NRCONR, SO, SO$_2$, NRSO$_2$, SO₂NR, NRSO₂NR, O, S, or NR; and each occurrence of $R^X$ is independently selected from R', halogen, NO₂, CN, OR', SR', N(R')₂, NR'C(O)R', NR'C(O)N(R')₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R';

each occurrence of $R^3$ and $R^4$ is independently selected from R, halogen, CN, OR, N(R)₂, SR, C(=O)R, CO₂R, CONR₂, NRC(=O)R, NRCO₂(C₁₋₆ aliphatic), OC(=O)R, SO₂R, S(=O)R, SO₂NR₂, or NRSO₂(C₁₋₆ aliphatic);

n is 0, 1, 2;

m is 0, 1, 2 or 3;

T is an optionally substituted C₁₋₄ alkylidene chain wherein one methylene unit of T is optionally replaced by O, NR, NRCO, NRCONR, NRCO₂, CO, CO₂, CONR, OC(O)NR, SO₂, SO₂NR, NRSO₂, NRSO₂NR, C(O)C(O), or C(O)CH₂C(O); q is 0 or 1;

$R^Z$ is R, CN, halogen, or Cy;

Cy is an optionally substituted aryl or heteroaryl group selected from a 5–6 membered monocyclic or an 8–10 membered bicyclic ring having 0–5 heteroatoms independently selected from nitrogen, oxygen, or sulfur; or is an optionally substituted group selected from a 3–8-membered saturated or partially unsaturated monocyclic ring having 0–3 heteroatoms independently selected from nitrogen, oxygen, or sulfur, or an 8–10-membered saturated or partially unsaturated bicyclic ring system having 0–5 heteroatoms independently selected from nitrogen, oxygen, or sulfur, wherein Cy is optionally substituted with up to five substituents selected from Z-$R^Y$; wherein Z is a bond or is a C₁–C₆ alkylidene chain non-adjacent methylene units of Q are optionally replaced by CO, CO₂, COCO, CONR, OCONR, NRNR, NRNRCO, NRCO, NRCO₂, NRCONR, SO, SO₂, NRSO₂, SO₂NR, NRSO₂NR, O, S, or NR; and each occurrence of $R^Y$ is independently selected from R', halogen, NO₂, CN, OR', SR', N(R')₂, NR'C(O)R', NR'C(O)N(R)₂, NR'CO₂R', C(O)R', CO₂R', OC(O)R', C(O)N(R')₂, OC(O)N(R')₂, SOR', SO₂R', SO₂N(R')₂, NR'SO₂R', NR'SO₂N(R')₂, C(O)C(O)R', or C(O)CH₂C(O)R';

each occurrence of R is independently selected from hydrogen or an optionally substituted C₁₋₈ aliphatic group, or two R on the same nitrogen are taken together with the nitrogen to form an optionally substituted 5–8 membered heterocyclyl or heteroaryl ring having 1–3 heteroatoms independently selected from nitrogen, oxygen, or sulfur; and each occurrence of R' is independently selected from hydrogen or an optionally substituted group selected from C₁₋₈ aliphatic, C₆₋₁₀ aryl, a heteroaryl ring having 5–10 ring atoms, or a heterocyclyl ring having 3–10 ring atoms, or wherein two R' on the same nitrogen are taken together with the nitrogen to form an optionally substituted 5–8 membered heterocyclyl or heteroaryl ring having 1–3 heteroatoms independently selected from nitrogen, oxygen, or sulfur, provided that when $R^Z$ is Cy, and Cy is an optionally substituted 5–6 membered monocyclic or an 8–10 membered bicyclic aryl ring having 0 heteroatoms, then q is 1.

2. The compound of claim 1, wherein one of $R^1$ or $R^2$ is $(U)_p$—$R^5$, and $R^5$ is an optionally substituted aryl or heteroaryl group selected from:

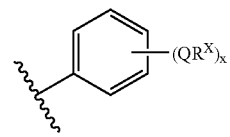

a-i

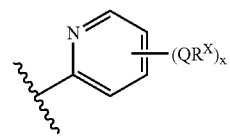

b-i

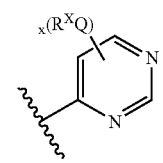

c-i

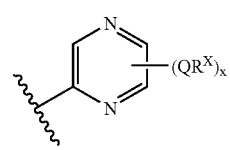

d-i

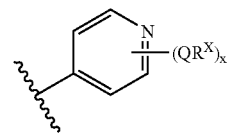

e-i

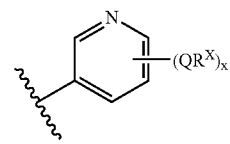

f-i

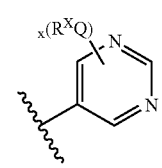

g-i

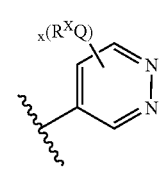

h-i

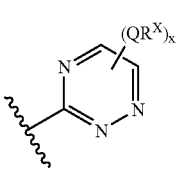

i-i

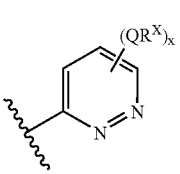

j-i

-continued
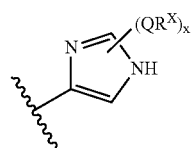 k-i
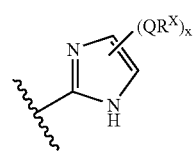 l-i
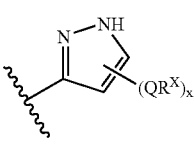 m-i
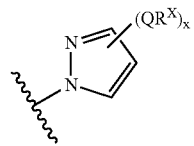 n-i
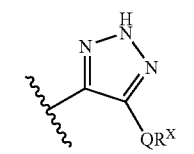 o-i
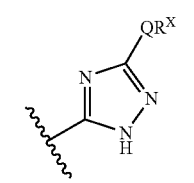 p-i
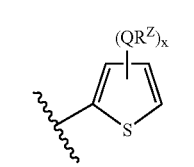 q-i
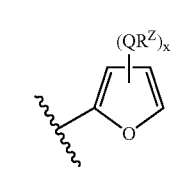 r-i
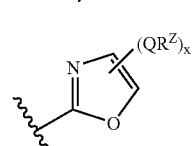 s-i
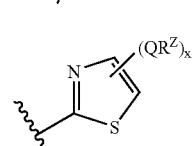 t-i
-continued
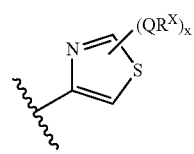 u-i
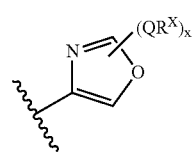 v-i
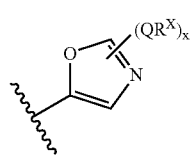 w-i
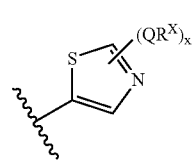 x-i
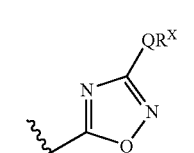 y-i
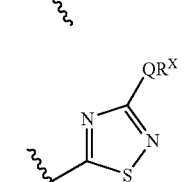 z-i
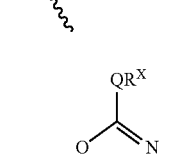 aa-i
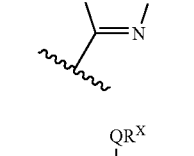 bb-i
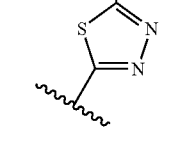 cc-i

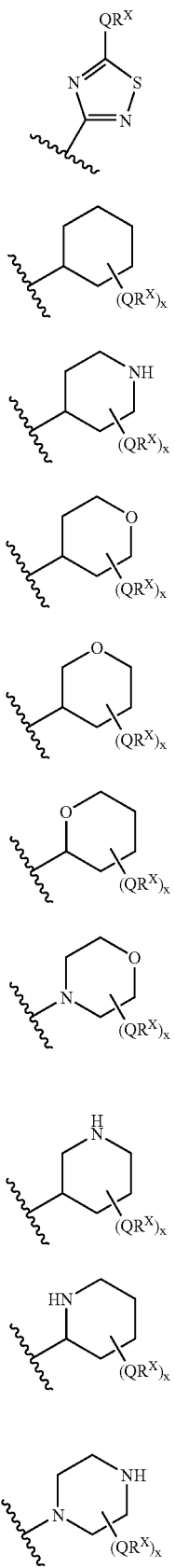
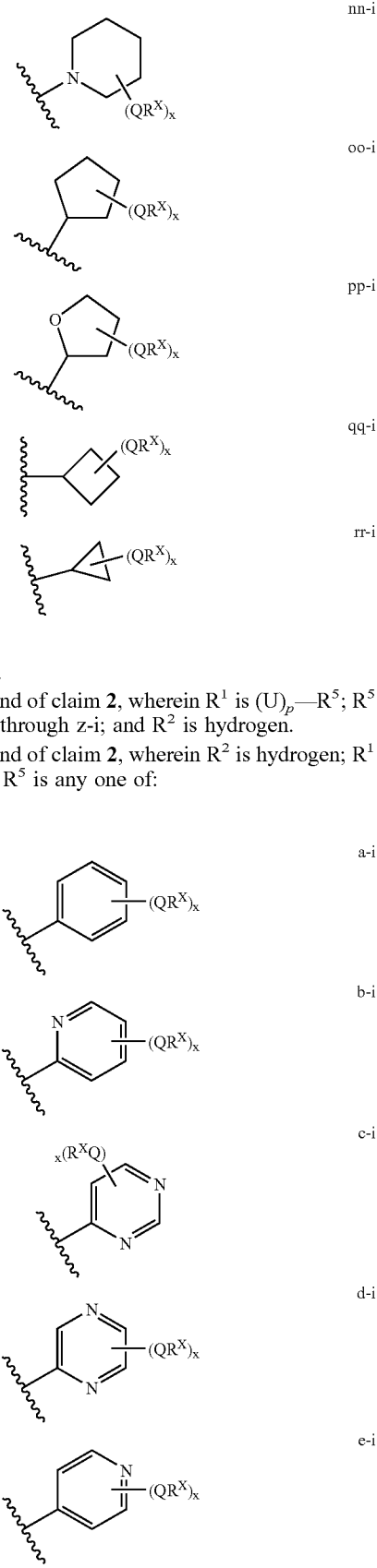
wherein x is 0–5.
3. The compound of claim 2, wherein $R^1$ is $(U)_p$—$R^5$; $R^5$ is any one of a-i through z-i; and $R^2$ is hydrogen.
4. The compound of claim 2, wherein $R^2$ is hydrogen; $R^1$ is $(U)_p$—$R^5$; and $R^5$ is any one of:

-continued

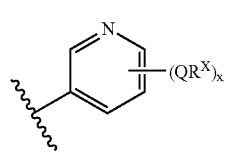
f-i

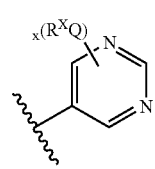
g-i

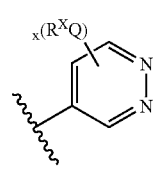
h-i

5. The compound of claim 2, wherein $R^2$ is hydrogen, and $R^1$ is $(U)_p$—$R^5$, wherein U and p are as defined generally above and herein, and $R^5$ is a-i, b-i, e-i, or f-i.

6. The compound of claim 2, wherein $R^2$ is hydrogen; $R^1$ is $(U)_p$—$R^5$; and $R^5$ is a-i.

7. The compound of claim 1, wherein p is 0 and $R^5$ is directly attached to the ring system.

8. The compound of claim 1, wherein p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—.

9. The compound of claim 1, wherein p is 1, U is —CH$_2$—, —CO—, —CO(CH$_2$)O—, —CO(CH$_2$)$_2$—, CO(NH)— or —CO(O)—.

10. The compound of claim 1, wherein $R^Z$ is Cy, and Cy is an optionally substituted group selected from:

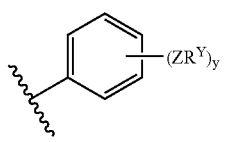
a-ii

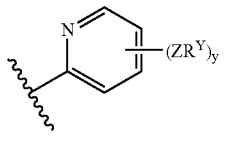
b-ii

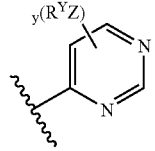
c-ii

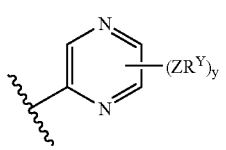
d-ii

-continued

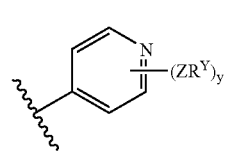
e-ii

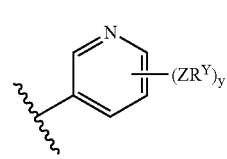
f-ii

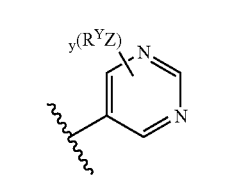
g-ii

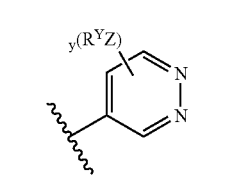
h-ii

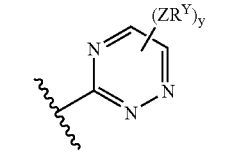
i-ii

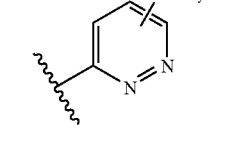
j-ii

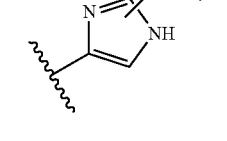
k-ii

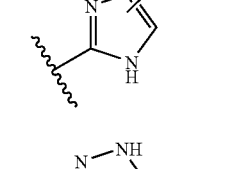
l-ii

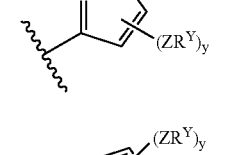
m-ii

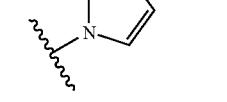
n-ii

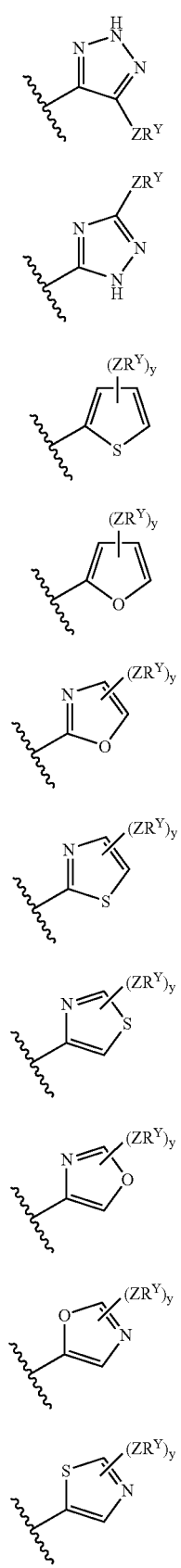
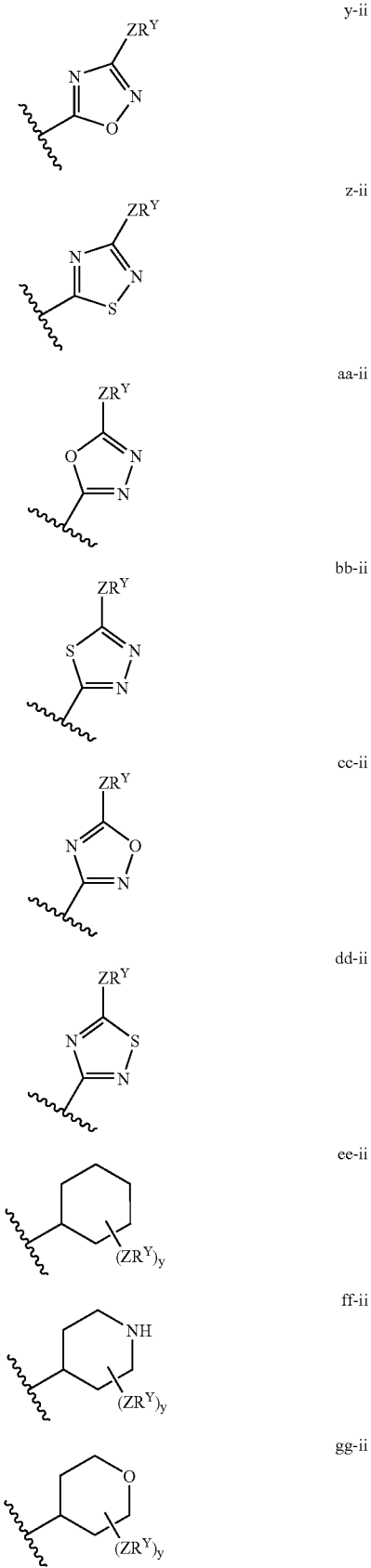

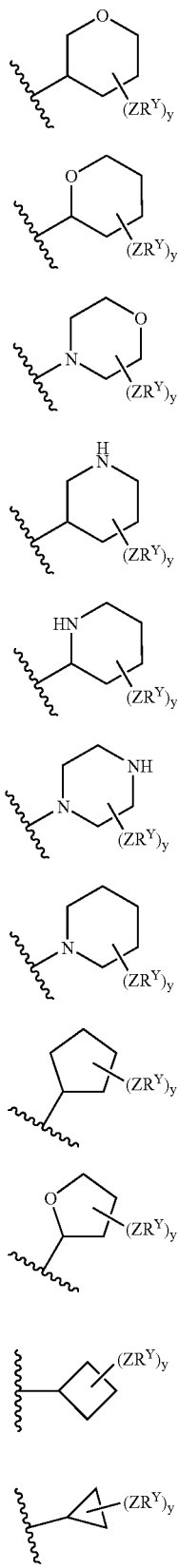

wherein y is 0–5.

11. The compound of claim 10, wherein Cy is a-ii, b-ii, c-ii, e-ii, f-ii, g-ii, or oo-ii.

12. The compound of claim 10, wherein Cy is any one of i-ii, j-ii, k-ii, l-ii, m-ii, n-ii, o-ii, p-ii, q-ii, r-ii, s-ii, t-ii, u-ii, v-ii, x-ii, y-ii, z-ii, aa-ii, bb-ii, cc-ii, dd-ii, ee-ii, ff-ii, gg-ii, hh-ii, ii-ii, jj-ii, kk-ii, ll-ii, mm-ii, nn-ii, oo-ii, pp-ii, qq-ii, or rr-ii.

13. The compound of claim 1, wherein q is 0 and T is absent.

14. The compound of claim 1, wherein q is 1 and T is selected from —CH$_2$—, —CH$_2$CH$_2$—, —CH$_2$CH$_2$CH$_2$—, —CH$_2$CH$_2$CH$_2$CH$_2$—, —C≡C—, —C=C—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—.

15. The compound of claim 1, wherein QR$^X$ and ZR$^Y$ groups are each independently halogen, CN, NO$_2$, or an optionally substituted group selected from C$_{1-4}$alkyl, aryl, aralkyl, —N(R')$_2$, CH$_2$N(R')$_2$, —OR', CH$_2$OR', —SR', CH$_2$SR',COOR', or —S(O)$_2$N(R')$_2$.

16. The compound of claim 1, wherein QR$^X$ and ZR$^Y$ groups are each independently Cl,Br, F, CN, COOH, —N(CH$_3$)$_2$, —OH, CH$_2$OH, SO$_2$NH$_2$, or an optionally substituted group selected from C$_{1-4}$ alkoxy, phenyl, phenyloxy, benzyl, or benzyloxy.

17. The compound of claim 1, wherein R$^3$ is selected from hydrogen or a C$_{1-4}$ alkyl group.

18. The compound of claim 1, wherein each occurrence of R$^3$ is hydrogen.

19. The compound of claim 1, wherein each occurrence of R$^4$ is selected from hydrogen, halo, O(C$_{1-4}$ alkyl), or a C$_{1-4}$ alkyl group.

20. The compound of claim 1, wherein each occurrence of R$^4$ is hydrogen.

21. The compound of claim 1, wherein R$^Z$ is Cy, and Cy is an optionally substituted 2-pyridyl, 3-pyridyl, 4-pyridyl, 4-pyrimdinyl, 5-pyrimidinyl, or tetrahydrofuranyl group and the compounds have one of the general formulae:

22. The compound of claim 21, wherein:

a) $R^2$ is hydrogen; $R^1$ is $(U)_p$—R, wherein p is 0, or p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and $R^5$ is any one of:

b) n is 0, 1, or 2, and each occurrence of $R^3$ is selected from hydrogen or a $C_{1-4}$ alkyl group;

c) m is 0, 1, 2, or 3, and each occurrence of $R^4$ is selected from hydrogen, halo, O($C_{1-4}$ alkyl), or a $C_{1-4}$ alkyl group;

d) q is 0, or q is 1 and T groups, when present, are selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and e) x is 0, 1, or 2, and y is 0, 1, or 2, and each occurrence of $QR^X$ and $ZR^Y$ is independently Cl, Br, F, CN, COOH, —N(CH$_3$)$_2$, —OH, CH$_2$OH, SO$_2$NH$_2$, or an optionally substituted group selected from $C_{1-4}$alkoxy, phenyl, phenyloxy, benzyl, or benzyloxy.

23. The compound of claim 21, wherein:

a) $R^2$ is hydrogen, and $R^1$ is $(U)_p$—$R^5$, wherein p is 0, or p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and $R^5$ is a-i, b-i, e-i, or f-i;

b) n is 0, 1, or 2, and each occurrence of $R^3$ is selected from hydrogen or a $C_{1-4}$ alkyl group;

c) m is 0, 1, 2, or 3, and each occurrence of $R^4$ is selected from hydrogen, halo, O($C_{1-4}$ alkyl), or a $C_{1-4}$ alkyl group;

d) q is 0, or q is 1 and T groups, when present, are selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and e) x is 0, 1, or 2, and y is 0, 1, or 2, and each occurrence of QR$^X$ and ZR$^Y$ is independently Cl, Br, F, CN, COOH, —N(CH$_3$)$_2$, —OH, CH$_2$OH, SO$_2$NH$_2$, or an optionally substituted group selected from C$_{1-4}$alkoxy, phenyl, phenyloxy, benzyl, or benzyloxy.

24. The compound of claim 21, wherein:

a) R$^2$ is hydrogen; R$^1$ is (U)$_p$—R$^5$, wherein R$^2$ is hydrogen; R$^1$ is (U)$_p$—R$^5$, wherein p is 0, or p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$—, NH—; and R$^5$ is a-i;

b) n is 0, 1, or 2, and each occurrence of R$^3$ is selected from hydrogen or a C$_{1-4}$ alkyl group;

c) m is 0, 1, 2, or 3, and each occurrence of R$^4$ is selected from hydrogen, halo, O(C$_{1-4}$ alkyl), or a C$_{1-4}$ alkyl group;

d) q is 0, or q is 1 and T groups, when present, are selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, —CO(CH$_2$)$_{0-2}$NH—; and e) x is 0, 1, or 2, and y is 0, 1, or 2, and each occurrence of QR$^X$ and ZR$^Y$ is independently Cl, Br, F, CN, COOH, —N(CH$_3$)$_2$, —OH, CH$_2$OH, SO$_2$NH$_2$, or an optionally substituted group selected from C$_{1-4}$alkoxy, phenyl, phenyloxy, benzyl, or benzyloxy.

25. The compound of claim 10, wherein a) R$^Z$ is Cy, and Cy is any one of b-ii, c-ii, d-ii, e-ii, f-ii, g-ii, h-ii, i-ii, j-ii, k-ii, l-ii, m-ii, n-ii, o-ii, p-ii, q-ii, r-ii, s-ii, t-ii, u-ii, v-ii, x-ii, y-ii, z-ii, aa-ii, bb-ii, cc-ii, dd-ii, ee-ii, ff-ii, gg-ii, hh-ii, ii-ii, jj-ii, kk-ii, ll-ii, mm-ii, nn-ii, oo-ii, pp-ii, qq-ii, or rr-ii;

b) R$^2$ is hydrogen; R$^1$ is (U)$_p$—R$^5$, wherein p is 0, or p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, CONH(CH$_2$)$_{0-2}$—, or —CO(CH$_2$)$_{0-2}$NH—; and R$^5$ is any one of:

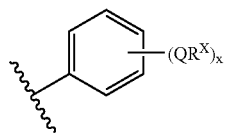
a-i

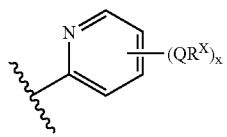
b-i

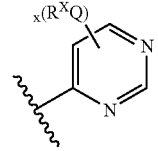
c-i

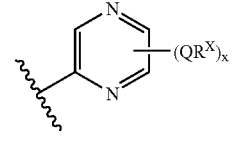
d-i

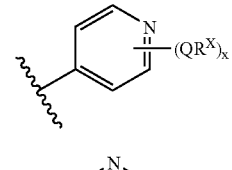
e-i

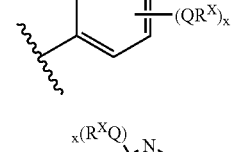
f-i

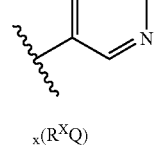
g-i

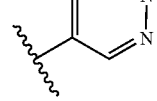
h-i c) n is 0, 1, or 2, and each occurrence of R$^3$ is selected from hydrogen or a C$_{1-4}$ alkyl group;

d) m is 0, 1, 2, or 3, and each occurrence of R$^4$ is selected from hydrogen, halo, O(C$_{1-4}$ alkyl), or a C$_{1-4}$ alkyl group;

e) q is 0, or q is 1 and T groups, when present, are selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and f) x is 0, 1, or 2, and y is 0, 1, or 2, and each occurrence of QR$^X$ and ZR$^Y$ is independently Cl, Br, F, CN, COOH, —N(CH$_3$)$_2$, —OH, CH$_2$OH, SO$_2$NH$_2$, or an optionally substituted group selected from C$_{1-4}$alkoxy, phenyl, phenyloxy, benzyl, or benzyloxy.

26. The compound of claim 1, wherein a) R$^Z$ is Cy, and Cy is any one of i-ii, j-ii, k-ii, l-ii, m-ii, n-ii, o-ii, p-ii, q-ii, r-ii, s-ii, t-ii, u-ii, v-ii, x-ii, y-ii, z-ii, aa-ii, bb-ii, cc-ii, dd-ii, ee-ii, ff-ii, gg-ii, hh-ii, ii-ii, jj-ii, kk-ii, ll-ii, mm-ii, nn-ii, oo-ii, pp-ii, qq-ii, or rr-ii;

b) R$^2$ is hydrogen; R$^1$ is (U)$_p$—R$^5$, wherein p is 0, or p is 1 and U is selected from —CH$_2$—, —CH$_2$CH$_2$—, —CH$_2$CH$_2$CH$_2$—, —CH$_2$CH$_2$CH$_2$CH$_2$—, —CO(CH$_2$)$_{0-2}$—, —CO(CH$_2$)$_{0-2}$O—, —CONH(CH$_2$)$_{0-2}$—, or —CO(CH$_2$)$_{0-2}$NH—; and R$^5$ is any one of:

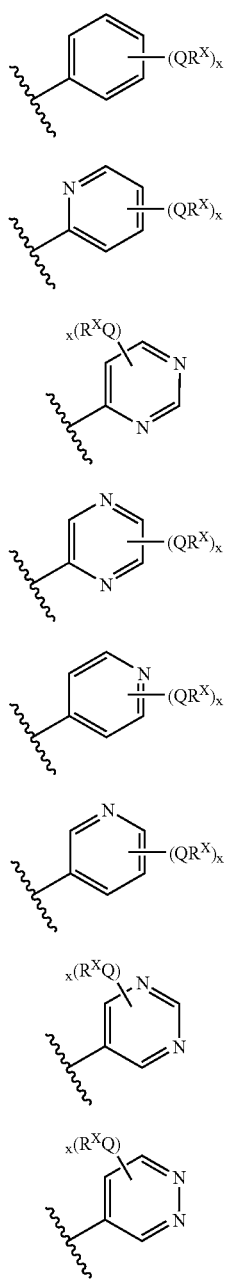

a-i
b-i
c-i
d-i
e-i
f-i
g-i
h-i c) n is 0, 1, or 2, and each occurrence of $R^3$ is selected from hydrogen or a $C_{1-4}$ alkyl group;
d) m is 0, 1, 2, or 3, and each occurrence of $R^4$ is selected from hydrogen, halo, $O(C_{1-4}$ alkyl), or a $C_{1-4}$ alkyl group;
e) q is 0, or q is 1 and T groups, when present, are selected from —$CH_2$—, —$CH_2CH_2$—, —$CH_2CH_2CH_2$—, —$CH_2CH_2CH_2CH_2$—, —$CO(CH_2)_{0-2}$—, —$CO(CH_2)_{0-2}O$—, —$CONH(CH_2)_{0-2}$—, or —$CO(CH_2)_{0-2}NH$—; and
f) x is 0, 1, or 2, and y is 0, 1, or 2, and each occurrence of $QR^X$ and $ZR^Y$ is independently Cl, Br, F, CN, COOH, —$N(CH_3)_2$, —OH, $CH_2OH$, $SO_2NH_2$, or an optionally substituted group selected from $C_{1-4}$alkoxy, phenyl, phenyloxy, benzyl, or benzyloxy.

27. The compound of claim 1, selected from:

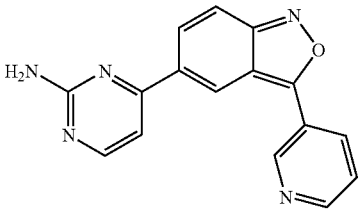

I-1

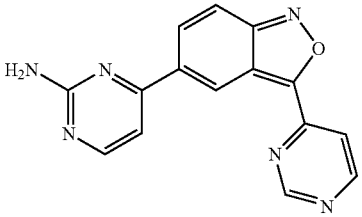

I-2

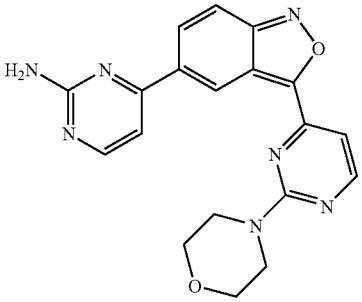

I-3

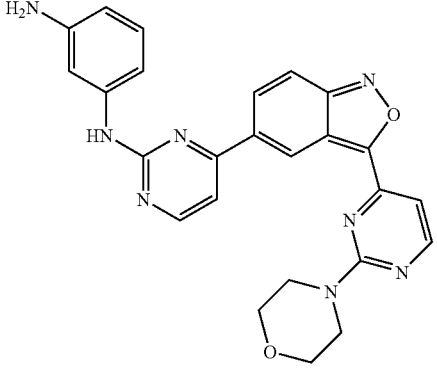

I-4

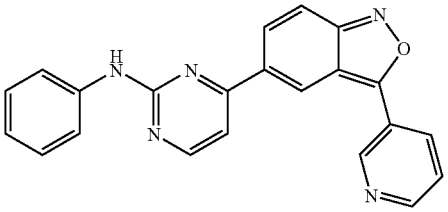

I-5

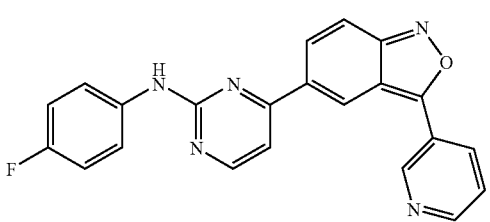

I-6

-continued
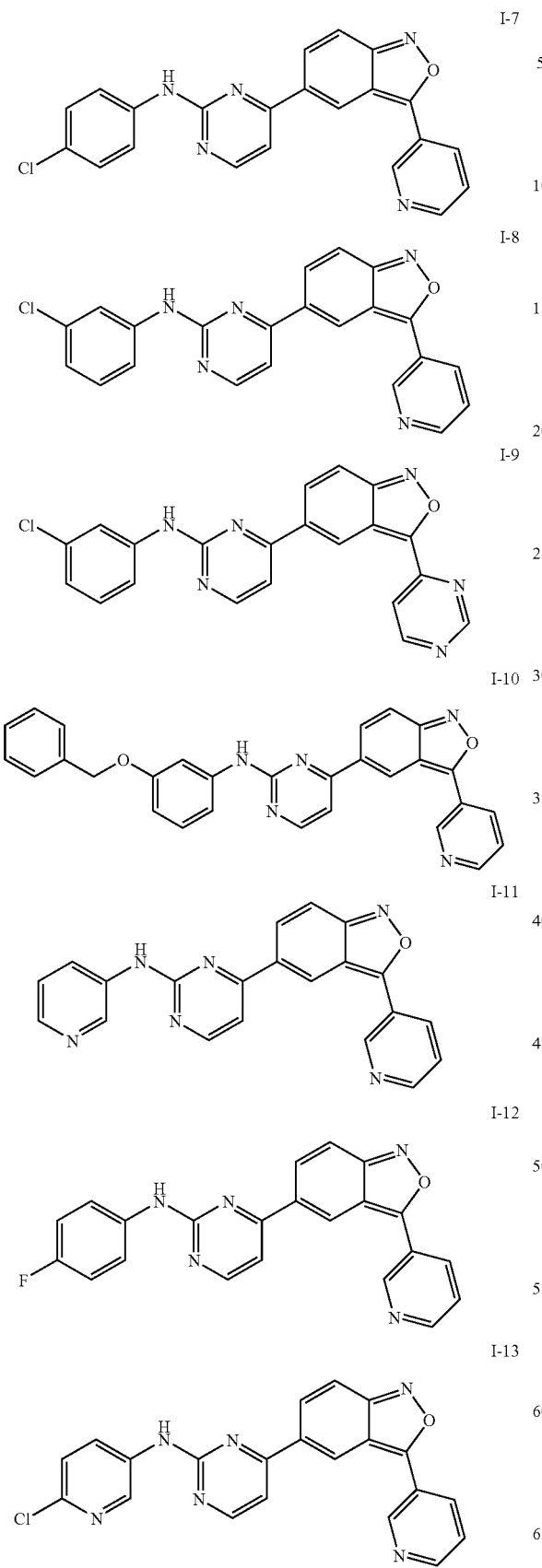
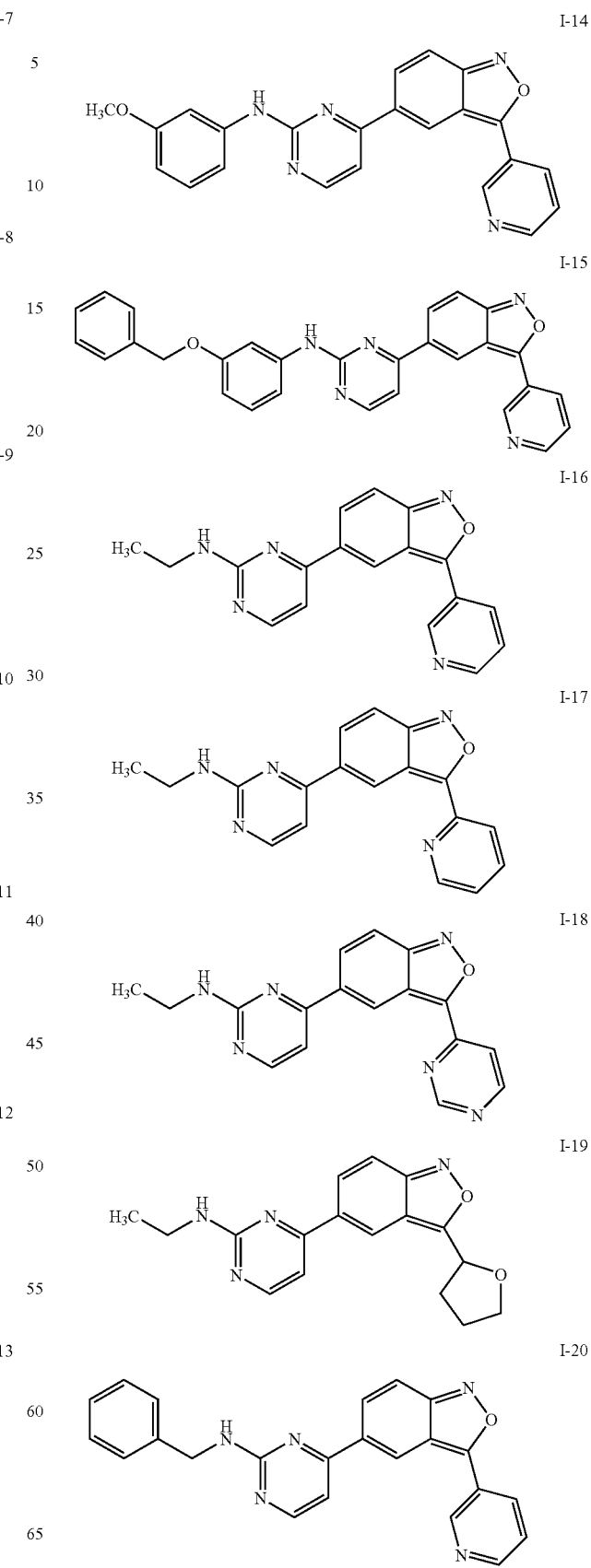

-continued
I-21
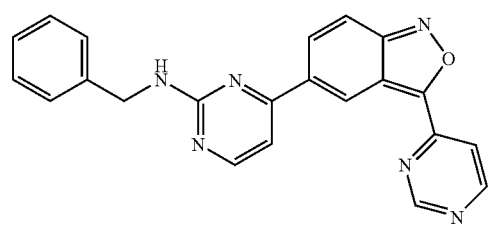
I-22
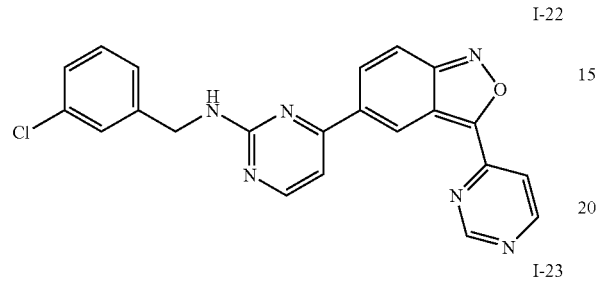
I-23
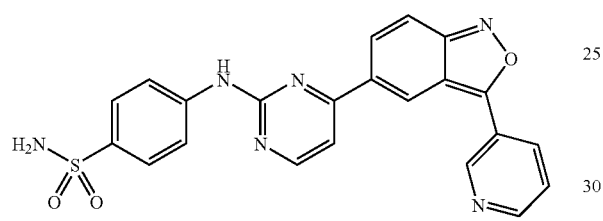
I-24
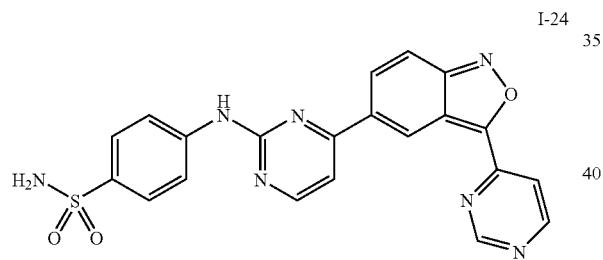
I-25
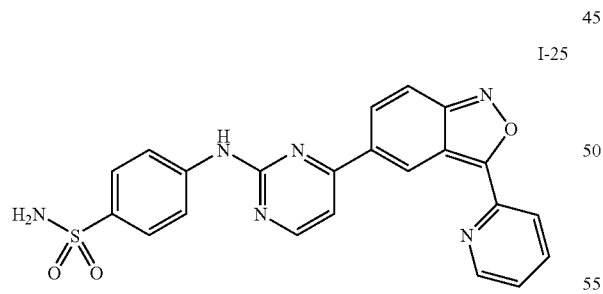
I-26
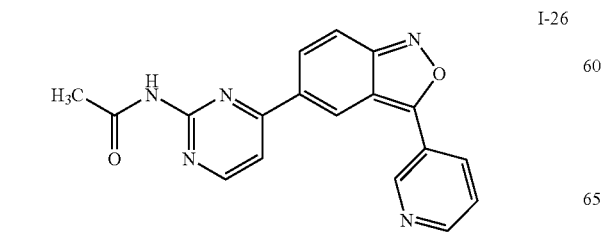
-continued
I-27
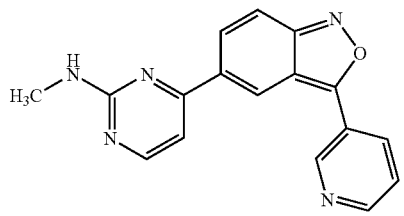
I-28
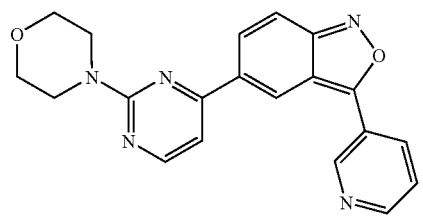
I-29
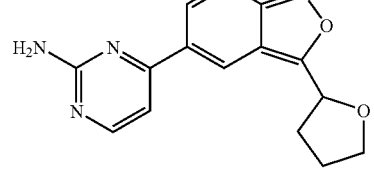
I-30
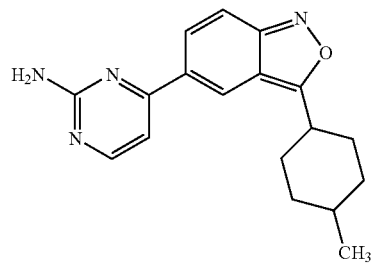
I-31
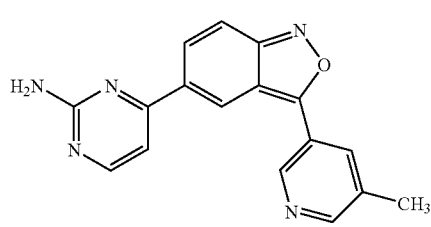
I-32
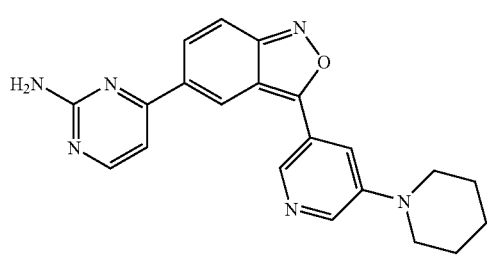

-continued

I-33
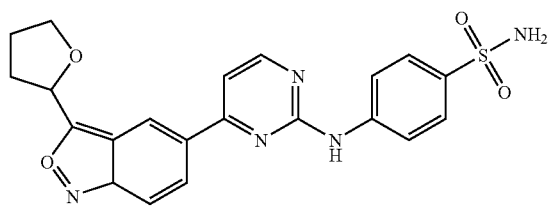

I-34
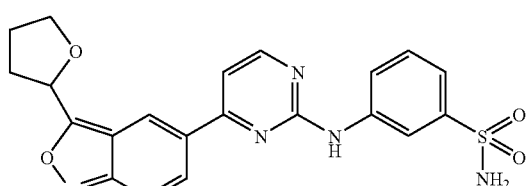

I-35
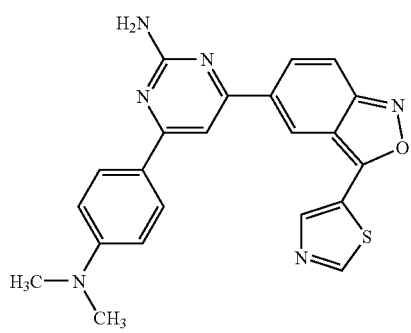

I-36
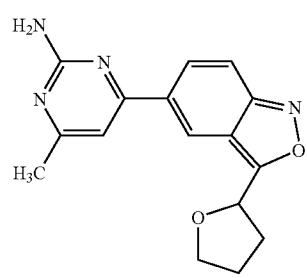

-continued

I-37
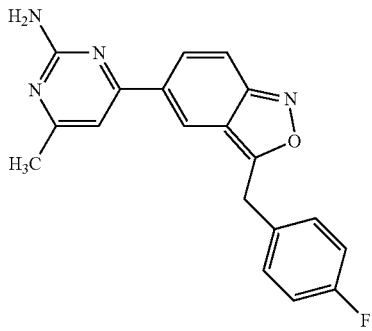

I-38
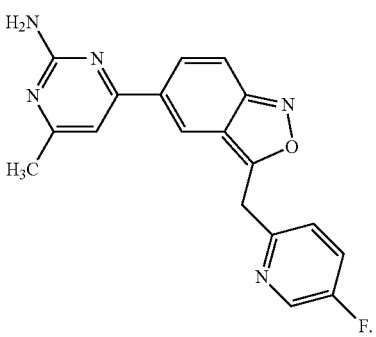

28. A composition comprising a compound of claim 1, and a pharmaceutically acceptable carrier or diluent.

29. The composition of claim 28, additionally comprising a therapeutic agent selected from an anti-flammatory agent, an immunomodulatory or immunosuppressive agent, or an agent for treating asthma.

30. A method of treating or lessening the severity of a disease or condition selected from rheumatoid arthritis, allergic or type I hypersensitivity reaction, asthma, transplant rejection or familial amyotrophic lateral selerosis (FALS), comprising the step of administering to a patient in need thereof
 a) a composition of claim 28; or
 b) a compound of claim 1.

31. The method of claim 30, comprising the additional step of administering to said patient an additional therapeutic agent selected from an anti-inflammatory agent, an immunomodulatory or immunosuppressive agent, or an agent for treating asthma, wherein:
 said additional therapeutic agent is appropriate for the disease being treated; and
 said additional therapeutic agent is administered together with said composition as a single dosage form or separately from said composition as part of a multiple dosage form.

* * * * *